US009167814B2

(12) United States Patent
Lange et al.

(10) Patent No.: US 9,167,814 B2
(45) Date of Patent: Oct. 27, 2015

(54) SURFACTANT PEROXYCARBOXYLIC ACID COMPOSITIONS

(71) Applicant: Ecolab USA Inc., St. Paul, MN (US)

(72) Inventors: Steven J. Lange, St. Paul, MN (US); Junzhong Li, Apple Valley, MN (US)

(73) Assignee: ECOLAB USA, INC., St. Paul, MN (US)

(*) Notice: Subject to any disclaimer, the term of this patent is extended or adjusted under 35 U.S.C. 154(b) by 0 days.

(21) Appl. No.: 14/513,298

(22) Filed: Oct. 14, 2014

(65) Prior Publication Data
US 2015/0031766 A1 Jan. 29, 2015

Related U.S. Application Data

(63) Continuation of application No. 12/792,142, filed on Jun. 2, 2010, now abandoned, which is a continuation of application No. 11/176,917, filed on Jul. 6, 2005, now Pat. No. 7,754,670.

(51) Int. Cl.
A01N 37/44 (2006.01)
A01N 37/36 (2006.01)
A23B 4/20 (2006.01)
A23B 7/154 (2006.01)
A23L 3/3508 (2006.01)
A61L 2/18 (2006.01)
A61L 9/16 (2006.01)
C11D 3/39 (2006.01)
C11D 3/48 (2006.01)
A01N 41/04 (2006.01)

(52) U.S. Cl.
CPC .............. A01N 37/44 (2013.01); A01N 37/36 (2013.01); A01N 41/04 (2013.01); A23B 4/20 (2013.01); A23B 7/154 (2013.01); A23L 3/3508 (2013.01); A61L 2/183 (2013.01); A61L 2/186 (2013.01); A61L 9/16 (2013.01); C11D 3/3945 (2013.01); C11D 3/48 (2013.01)

(58) Field of Classification Search
CPC ...................................... A01N 37/44
USPC ................. 510/302; 426/321, 331, 652
See application file for complete search history.

(56) References Cited

U.S. PATENT DOCUMENTS

| 2,512,640 | A | | 6/1950 | Greenspan et al. |
| 2,813,896 | A | * | 11/1957 | Krimm ........................ 562/2 |
| 2,833,813 | A | | 5/1958 | Wallace |
| 3,122,417 | A | | 2/1964 | Blaser et al. |
| 3,248,281 | A | | 4/1966 | Goodenough |
| 3,350,265 | A | | 10/1967 | Rubinstein et al. |
| 3,514,278 | A | | 5/1970 | Brink, Jr. |
| 3,895,116 | A | | 7/1975 | Herting et al. |
| 3,929,678 | A | | 12/1975 | Laughlin et al. |
| 3,996,386 | A | | 12/1976 | Malkki et al. |
| 4,041,149 | A | | 8/1977 | Gaffar et al. |
| 4,049,556 | A | * | 9/1977 | Tujimoto et al. .................. 252/3 |
| 4,051,058 | A | | 9/1977 | Bowing et al. |
| 4,051,059 | A | | 9/1977 | Bowing |
| 4,119,660 | A | * | 10/1978 | Hutchins ........................ 562/6 |
| 4,129,517 | A | | 12/1978 | Eggensperger et al. |
| 4,191,660 | A | | 3/1980 | Schreiber et al. |
| 4,233,235 | A | * | 11/1980 | Camden et al. .................. 562/6 |
| 4,244,884 | A | | 1/1981 | Hutchins et al. |
| 4,289,728 | A | | 9/1981 | Peel et al. |
| 4,321,157 | A | | 3/1982 | Harris et al. |
| 4,337,213 | A | * | 6/1982 | Marynowski et al. ............ 562/6 |
| 4,370,199 | A | | 1/1983 | Orndorff |
| 4,404,040 | A | * | 9/1983 | Wang ........................ 134/22.14 |
| 4,477,438 | A | | 10/1984 | Willcockson et al. |
| 4,478,683 | A | | 10/1984 | Orndorff |
| 4,501,681 | A | | 2/1985 | Groult et al. |
| 4,529,534 | A | | 7/1985 | Richardson |
| 4,557,898 | A | | 12/1985 | Greene et al. |
| 4,566,980 | A | | 1/1986 | Smith |
| 4,591,565 | A | | 5/1986 | Branner-Jorgensen et al. |
| 4,592,488 | A | | 6/1986 | Simon et al. |
| 4,613,452 | A | | 9/1986 | Sanderson |
| 4,655,781 | A | | 4/1987 | Hsieh et al. |
| 4,659,494 | A | | 4/1987 | Soldanski et al. |
| 4,666,622 | A | | 5/1987 | Martin et al. |
| 4,683,618 | A | | 8/1987 | O'Brien |
| 4,704,404 | A | | 11/1987 | Sanderson |
| 4,715,980 | A | | 12/1987 | Lopes et al. |
| 4,738,840 | A | | 4/1988 | Simon et al. |
| 4,802,994 | A | | 2/1989 | Mouche et al. |
| 4,834,900 | A | | 5/1989 | Soldanski et al. |

(Continued)

FOREIGN PATENT DOCUMENTS

| CA | 2181416 | 1/1997 |
| DE | 3003875 | 8/1981 |
| DE | 3543500 | 6/1987 |
| DE | 3906044 | 8/1990 |
| DE | 19751391 | 7/1998 |
| DK | 9300538 | 11/1994 |
| EP | 0125781 | 11/1984 |
| EP | 0140648 | 5/1985 |
| EP | 0167375 | 1/1986 |
| EP | 0186052 | 7/1986 |

(Continued)

OTHER PUBLICATIONS

Systems: A Review, A Journal of Food Protection, vol. 55, No. 2, pp. 133-140. Feb. 28, 1992.
Eggensperger, H., "Disinfectants Based on Peracid-Splitting Compounds," Zbl. Bakt. Hyg., I. Abt. Orig. B, vol. 168, pp. 517-524. Dec. 31, 1979.

(Continued)

Primary Examiner — Nicole M Buie-Hatcher
Assistant Examiner — M. Reza Asdjodi
(74) Attorney, Agent, or Firm — McKee, Voorhees & Sease, PLC

(57) ABSTRACT

The present invention relates to compositions including surfactant peroxycarboxylic acid, methods for making these compositions, and methods for reducing the population of a microorganism.

24 Claims, 1 Drawing Sheet

(56) References Cited

U.S. PATENT DOCUMENTS

| | | | |
|---|---|---|---|
| 4,865,752 A | 9/1989 | Jacobs | |
| 4,900,721 A | 2/1990 | Bansemir et al. | |
| 4,906,617 A | 3/1990 | Jacquet et al. | |
| 4,908,306 A | 3/1990 | Lorinez | |
| 4,917,815 A | 4/1990 | Beilfuss et al. | |
| 4,923,677 A | 5/1990 | Simon et al. | |
| 4,937,066 A | 6/1990 | Vlock | |
| 4,943,414 A | 7/1990 | Jacobs et al. | |
| 4,945,110 A | 7/1990 | Brokken et al. | |
| 4,996,062 A | 2/1991 | Lehtonen et al. | |
| 4,997,571 A | 3/1991 | Roensch et al. | |
| 4,997,625 A | 3/1991 | Simon et al. | |
| 5,004,760 A | 4/1991 | Patton et al. | |
| 5,010,109 A | 4/1991 | Inoi | |
| 5,015,408 A | 5/1991 | Reuss | |
| 5,043,176 A | 8/1991 | Bycroft et al. | |
| 5,069,286 A | 12/1991 | Roensch et al. | |
| 5,078,896 A | 1/1992 | Rorig et al. | |
| 5,084,239 A | 1/1992 | Moulton et al. | |
| 5,093,140 A | 3/1992 | Watanabe | |
| 5,114,178 A | 5/1992 | Baxter | |
| 5,114,718 A | 5/1992 | Damani | |
| 5,122,538 A | 6/1992 | Lokkesmoe et al. | |
| 5,129,824 A | 7/1992 | Keller | |
| 5,130,124 A | 7/1992 | Merianos et al. | |
| 5,139,788 A | 8/1992 | Schmidt | |
| 5,168,655 A | 12/1992 | Davidson et al. | |
| 5,176,899 A | 1/1993 | Montgomery | |
| 5,184,471 A | 2/1993 | Losacco et al. | |
| 5,200,189 A | 4/1993 | Oakes et al. | |
| 5,208,057 A | 5/1993 | Greenley et al. | |
| 5,234,703 A | 8/1993 | Guthery | |
| 5,234,719 A | 8/1993 | Richter et al. | |
| 5,266,587 A | 11/1993 | Sankey et al. | |
| 5,268,003 A | 12/1993 | Coope et al. | |
| 5,292,447 A | 3/1994 | Venturello et al. | |
| 5,314,687 A | 5/1994 | Oakes et al. | |
| 5,320,805 A | 6/1994 | Kramer et al. | |
| 5,336,500 A | 8/1994 | Richter et al. | |
| 5,364,650 A | 11/1994 | Guthery | |
| 5,391,324 A | 2/1995 | Reinhardt et al. | |
| 5,409,713 A | 4/1995 | Lokkesmoe et al. | |
| 5,419,908 A | 5/1995 | Richter et al. | |
| 5,435,808 A | 7/1995 | Holzhauer et al. | |
| 5,436,008 A | 7/1995 | Richter et al. | |
| 5,437,868 A | 8/1995 | Oakes et al. | |
| 5,463,112 A * | 10/1995 | Sankey et al. | 562/2 |
| 5,466,825 A | 11/1995 | Carr et al. | |
| 5,489,434 A | 2/1996 | Oakes et al. | |
| 5,489,706 A | 2/1996 | Revell | |
| 5,494,588 A | 2/1996 | LaZonby | |
| 5,508,046 A | 4/1996 | Cosentino et al. | |
| 5,512,309 A | 4/1996 | Bender et al. | |
| 5,527,898 A | 6/1996 | Bauer et al. | |
| 5,545,343 A | 8/1996 | Brougham et al. | |
| 5,545,374 A | 8/1996 | French et al. | |
| 5,578,134 A * | 11/1996 | Lentsch et al. | 134/3 |
| 5,591,706 A | 1/1997 | Ploumen | |
| 5,595,967 A | 1/1997 | Miracle et al. | |
| 5,597,790 A | 1/1997 | Thoen | |
| 5,616,335 A | 4/1997 | Nicolle et al. | |
| 5,616,616 A | 4/1997 | Hall et al. | |
| 5,624,634 A | 4/1997 | Brougham | |
| 5,632,676 A | 5/1997 | Kurschner et al. | |
| 5,641,530 A | 6/1997 | Chen | |
| 5,656,302 A | 8/1997 | Cosentino et al. | |
| 5,658,467 A | 8/1997 | LaZonby et al. | |
| 5,658,595 A | 8/1997 | Van Os | |
| 5,674,538 A | 10/1997 | Lokkesmoe et al. | |
| 5,674,828 A | 10/1997 | Knowlton et al. | |
| 5,683,724 A | 11/1997 | Hei et al. | |
| 5,712,239 A | 1/1998 | Knowlton et al. | |
| 5,718,910 A | 2/1998 | Oakes et al. | |
| 5,720,983 A | 2/1998 | Malone | |
| 5,756,139 A | 5/1998 | Harvey et al. | |
| 5,785,867 A | 7/1998 | LaZonby et al. | |
| 5,840,343 A | 11/1998 | Hall, II et al. | |
| 5,851,483 A | 12/1998 | Nicolle et al. | |
| 5,891,392 A | 4/1999 | Monticello et al. | |
| 5,900,256 A | 5/1999 | Scoville, Jr. et al. | |
| 5,902,619 A | 5/1999 | Rubow et al. | |
| 5,911,981 A * | 6/1999 | Dahms et al. | 424/70.19 |
| 5,962,392 A | 10/1999 | Revell et al. | |
| 5,968,539 A | 10/1999 | Beerse et al. | |
| 5,989,611 A | 11/1999 | Stemmler, Jr. et al. | |
| 5,998,358 A | 12/1999 | Herdt et al. | |
| 6,008,405 A | 12/1999 | Gray et al. | |
| 6,010,729 A | 1/2000 | Gutzmann et al. | |
| 6,024,986 A | 2/2000 | Hei | |
| 6,028,104 A | 2/2000 | Schmidt et al. | |
| 6,033,705 A | 3/2000 | Isaacs | |
| 6,039,992 A | 3/2000 | Compadre et al. | |
| 6,049,002 A | 4/2000 | Mattila et al. | |
| 6,080,712 A | 6/2000 | Revell et al. | |
| 6,096,226 A | 8/2000 | Fuchs et al. | |
| 6,096,266 A | 8/2000 | Duroselle | |
| 6,096,348 A | 8/2000 | Miner et al. | |
| 6,103,286 A | 8/2000 | Gutzmann et al. | |
| 6,111,963 A | 8/2000 | Thompson, III | |
| 6,113,963 A | 9/2000 | Gutzmann et al. | |
| 6,165,483 A | 12/2000 | Hei et al. | |
| 6,183,807 B1 * | 2/2001 | Gutzmann et al. | 426/652 |
| 6,238,685 B1 | 5/2001 | Hei et al. | |
| 6,257,253 B1 * | 7/2001 | Lentsch et al. | 134/25.2 |
| 6,274,542 B1 | 8/2001 | Carr et al. | |
| 6,302,968 B1 * | 10/2001 | Baum et al. | 134/30 |
| 6,395,703 B2 | 5/2002 | Scepanski | |
| 6,451,746 B1 | 9/2002 | Moore et al. | |
| 6,489,281 B1 | 12/2002 | Smith et al. | |
| 6,514,556 B2 | 2/2003 | Hilgren et al. | |
| 6,545,047 B2 | 4/2003 | Gutzmann et al. | |
| 6,627,593 B2 | 9/2003 | Hei et al. | |
| 6,627,657 B1 | 9/2003 | Hilgren et al. | |
| 6,630,439 B1 | 10/2003 | Norwood et al. | |
| 6,635,286 B2 | 10/2003 | Hei et al. | |
| 6,638,902 B2 | 10/2003 | Tarara et al. | |
| 6,674,538 B2 | 1/2004 | Takahashi | |
| 2002/0012650 A1 * | 1/2002 | Klein | 424/70.28 |
| 2002/0128312 A1 * | 9/2002 | Hei et al. | 514/529 |
| 2003/0087786 A1 | 5/2003 | Hei et al. | |
| 2003/0199583 A1 | 10/2003 | Gutzmann et al. | |
| 2004/0002616 A1 | 1/2004 | Preto et al. | |
| 2004/0121917 A1 * | 6/2004 | Pakulski | 507/239 |
| 2005/0151117 A1 | 7/2005 | Man et al. | |
| 2007/0010420 A1 * | 1/2007 | Lange et al. | 510/376 |

FOREIGN PATENT DOCUMENTS

| | | |
|---|---|---|
| EP | 0195619 | 9/1986 |
| EP | 0233731 | 8/1987 |
| EP | 0242990 | 10/1987 |
| EP | 0361955 | 4/1990 |
| EP | 0404293 | 12/1990 |
| EP | 0460962 | 12/1991 |
| EP | 0461700 | 12/1991 |
| EP | 0569066 | 11/1993 |
| EP | 0603329 | 6/1994 |
| EP | 0667392 | 8/1995 |
| EP | 0779357 | 6/1997 |
| EP | 0805198 | 11/1997 |
| EP | 0843001 | 5/1998 |
| EP | 0967203 | 12/1999 |
| EP | 0985349 | 3/2000 |
| EP | 1382666 | 1/2004 |
| FR | 2321301 | 3/1977 |
| FR | 2324626 | 4/1977 |
| FR | 2578988 | 9/1986 |
| GB | 1494109 | 12/1977 |
| GB | 1570492 | 7/1980 |
| GB | 2182051 | 5/1987 |
| GB | 2187958 | 9/1987 |
| GB | 2207354 | 2/1989 |
| GB | 2255507 | 11/1992 |
| GB | 2257630 | 1/1993 |

(56) References Cited

FOREIGN PATENT DOCUMENTS

| | | |
|---|---:|---|
| GB | 2353800 | 3/2001 |
| JP | 731210 | 2/1995 |
| JP | 7258005 | 10/1995 |
| LU | 78568 | 4/1978 |
| NL | 9201631 | 9/1992 |
| RU | 210447 | 1/1998 |
| WO | 9118876 | 12/1991 |
| WO | 9301716 | 2/1993 |
| WO | 9406294 | 3/1994 |
| WO | 9414321 | 7/1994 |
| WO | 9415465 | 7/1994 |
| WO | 9421122 | 9/1994 |
| WO | 9423575 | 10/1994 |
| WO | 9534537 | 12/1995 |
| WO | 9630474 | 10/1996 |
| WO | 9731092 | 8/1997 |
| WO | 9731093 | 8/1997 |
| WO | 9828267 | 7/1998 |
| WO | 9951095 | 10/1999 |
| WO | 0018870 | 4/2000 |
| WO | 0147359 | 7/2001 |
| WO | 0203799 | 1/2002 |
| WO | 02054866 | 7/2002 |
| WO | 02060280 | 8/2002 |
| WO | 03080782 | 10/2003 |
| WO | 2004043162 | 5/2004 |

OTHER PUBLICATIONS

Focus on Interox, Effluent +Water Treatment Journal. Aug. 31, 1979.
Fraser, J., "Novel applications of peracetic acid in industrial disinfection," Specialty Chemicals, vol. 7, No. 3 pp. 178, 180, 182, 184, 186. Dec. 31, 1987.
FSTA abstract, accession No. 1999(10):C1223, abstracting: Journal of Food Protection, vol. 62, No. 7, pp. 761-765 (1 page. Dec. 31, 1999.
FSTA abstract accession No. 2000(06):J1220, abstracting: Dairy, Food and Environmental Sanitation, vol. 19, No. 12, pp. 842-847 (1 page). Dec. 31, 1999.
Greenspan, F. et al., "The Application of Peracetic Acid Germicidal Washes to Mold Control of Tomatoes," Food Technology, vol. 5, No. 3, pp. 95-97. Mar. 31, 1951.
Han, B. et al., "Destruction of Bacterial Spores on Solid Surfaces," Journal of Food Processing and Preservation, vol. 4, Nos. 1-2, pp. 95-110. Dec. 31, 1980.
Heinemann, P., "The Germicidal Efficiency of Commercial Preparations of Hydrogen Peroxid," The Journal of the American Medical Association, vol. LX, No. 21, pp. 1603-1606. Jan. 31, 1913.
Hilgren, J. et al., U.S. Appl. No. 09/614,631, filed Jul. 12, 2000.
Hutchings, I. et al., "Comparative Evaluation of the Bactericidal Efficiency of Peracetic Acid, Quaternaries, and Chlorine-Containing Compounds," Presented at the 49th General Meeting of the Society of American Bacteriologists, (Abstract), pp. 50-51. May 17, 1949.
Interox Chemicals Ltd. product brochure entitled: OXYMASTER Peracetic Acid 12%. (year unknown).
Interox Chemicals Ltd. Product brochure entitled: PROXITANE 4002 Peracetic Acid 36-40%. (year unknown).
Jager, P. et al., "Peracetic acid as a disinfectant in breweries and soft drink factories," Mitt Versuch. Gaorung. Wien., vol. 34, pp. 32-36. Dec. 31, 1980.
Kim, J. et al., "Cetylpyridinium Chloride (CPC) Treatment on Poultry Skin to Reduce Attached Salmonella," Journal of Food Protection, vol. 59, No. 3, pp. 322-326. Dec. 31, 1995.
Kunzmann, T., "Investigations on the disinfecting action of hydrogen peroxides," Fortschr. Med., vol. 52, No. 16, pp. 357-359. Dec. 31, 1934.
Laska, M. et al., "Odor structure-activity relationships of carboxylic acids correspond between squirrel monkeys and humans," Am .J. Physio., vol. 274, pp. R1639-R1645. Dec. 31, 1998.
Lillard, H., "Bacterial Cell Characteristics and Conditions Influencing their Adhesion to Poultry Skin," Journal of Food Protection, vol. 48, No. 9, pp. 803-807. Sep. 30, 1958.
Lillard, H., "Factors Affecting the Persistence of Salmonella During the Processing of Poultry," Journal of Food Protection, vol. 52, No. 11, pp. 829-832. Nov. 30, 1989.
Tamblyn, K. et al., "Bactericidal Activity of Organic Acids against *Salmonella typhimurium* Attached to Broiler Chicken Skin," Journal of Food Protection, vol. 60, No. 6, pp. 629-633. Dec. 31, 1997.
Taylor, J. et al., "A comparison of the bactericidal efficacy of 18 disinfectants used in the food industry against *Escherichia coli* O157:H7 and Pseudomonas aeruginosa at 10 and 20C," Journal of Applied Microbiology, vol. 87, pp. 718-725. Dec. 31, 1999.
Towle, G. et al., "Pectin," Industrial Gums polysaccharides and Their Derivatives, Second Edition, Ch. XIX, pp. 429-444. (year unknown).
Xiong, H. et al., "Spraying Chicken Skin with Selected Chemicals to Reduce Attached *Salmonella typhimurium*," Journal of Food Protection, vol. 61, No. 3, pp. 272-275. Jun. 2, 2010.
Yoshpe-Purer, Y. et al., "Disinfection of Water by Hydrogen Peroxide," Health Laboratory Science, vol. 5, No. 4, pp. 233-238. Oct. 31, 1968.
Application Guide for Household & Industrial markets, McIntyre Group Ltd. Dec. 31, 2002.
"Emery Fatty and Dibasic Acids Specifications and Characteristics", Emery Industries, Bulletin 145. Oct. 31, 1983.
Abstract: "Indirect food additives: adjuvants, production aids, and sanitizers", Fed. Register, 61 (108), 28051-28053, 1 pages. Jun. 4, 1996.
Armak Chemicals, "NEO-FAT Fatty Acids", Akzo Chemicals Inc., Bulletin No. 86-17. Dec. 31, 1986.
Baldry, M. et al., "Disinfection of Sewage Effluent with Peracetic Acid," Wat. Sci. Tech., vol. 21, No. 3, pp. 203-206. Dec. 31, 1989.
Baldry, M. et al., "Disinfection with peroxygens," Industrial Biocides, edited by K.R. Payne, New York, John Wiley & Sons, pp. 91-116. Dec. 31, 1988.
Baldry, M., "The bactericidal, fungicidal and sporicidal properties of hydrogen peroxide and peracetic acid", Journal of Applied Bacteriology, vol. 54, pp. 417-423. Dec. 31, 1983.
Bayliss, C. et al., "The Synergistic Killing of Spores of Bacillus Subtilis by Hydrogen Peroxide and Ultra-Violet Light Irradiation", FEMS Microbiology Letters, vol. 5, pp. 331-333. Dec. 31, 1979.
Bell, K. et al., "Reduction of foodborne micro-organisms on beef carcass tissue using acetic acid, sodium bicarbonate, and hydrogen peroxide spray washes", Food Microbiology, vol. 14, pp. 439-448. Dec. 31, 1997.
Beuchat, L., "Surface Disinfection of Raw Produce", Dairy, Food and Environmental Sanitation, vol. 12, No. 1, pp. 6-9. Jan. 31, 1992.
Block, S., "Peroxygen Compounds", Disinfection, Sterilization and Preservation, Fifth Edition, Chapter 9, pp. 185-204. Dec. 31, 2001.
Block, S., "Peroxygen Compounds", Disinfection, Sterilization and Preservation, Fourth Edition, Chapter 9, pp. 167-181. Dec. 31, 1991.
Breen, P. et al., "Elimination of Salmonella Contamination from Poultry Tissues by Cetylpyridinium Chloride Solutions", Journal of Food Protection, vol. 60, No. 9, pp. 1019-1021. Dec. 31, 1997.
Breen, P. et al., "Quaternary Ammonium Compounds Inhibit and Reduce the Attachment of Viable *Salmonella typimurium* to Poultry Tissues," Journal of Food Science, vol. 60, No. 6, pp. 1191-1196. Dec. 31, 1995.
Brown, G. et al., "Use of Xanthomonas-campestris pv-vesicatoria to Evalute Surface Disinfectants for Canker Quarantine Treatment of Citrus Fruit," Plant Disease, pp. 319-323. Apr. 30, 1987.
Computer search results—Level 1—5 patents. Mar. 31, 1994.
Computer search results from Ecolab Information Center. Jun. 30, 1998.
International Search Report dated Dec. 27, 2002.
International Search Report dated Jan. 30, 2002.
International Search Report (PCT/US2005/000147), dated Jul. 4, 2005.
International Search Report (PCT/US2005/000149), dated Jun. 28, 2005.
International Search Report (PCT/US2005/000231), dated Jun. 28, 2005.
International Search Report, dated Jun. 3, 2002.
International Search Report, dated May 3, 2005.
International Search Report mailed Nov. 3, 2006.

(56) References Cited

OTHER PUBLICATIONS

Cords, B., "New Peroxyacetic Acid Sanitizer," Proceedings, Twenty-Third Convention, Institute of Brewing, Sydney Australia, pp. 165-169. Dec. 31, 1995.

Dickens, J. et al., "Effects of Acetic Acid and Hydrogen Peroxide Application During Defeathering on the Microbiological Quality of Broiler Carcasses Prior to Evisceration," Poultry Science, vol. 76, pp. 657-660. Dec. 31, 1997.

Dickens, J. et al., "The Effect of Acetic Acid and Air Injection on Appearance, Moisture Pick-Up, Microbiological Quality, and *Salmonella* Incidence on Processed Poultry Carcasses," Poultry Science, vol. 73, pp. 582-586. Dec. 31, 1994.

Dickens, J. et al., "The Effect of an Acetic Acid Dip on Carcass Appearance, Microbiological Quality, and Cooked Breast Meat Texture and Flavor," Poultry Science, vol. 73, pp. 576-581. Dec. 31, 1994.

Dickens, J. et al., "The Effects of Extended Chilling Times with Acetic Acid on the Temperature and Microbiological Quality of Processed Poultry Carcasses," Poultry Science, vol. 74, pp. 1044-1048. Dec. 31, 1995.

Dickson, J. et al., "Microbiological Decontamination of Food Animal Carcasses by Washing and Sanitizing Systems: A Review", Journal of Food Protections, vol. 55, No. 2, pp. 133-140. Feb. 28, 1992.

Lion, C. et al., "New decontaminants. Reaction of peroxyacid esters with toxic insecticides", Bull. Soc. Chim. Belg., vol. 100, No. 7, pp. 555-559. Dec. 31, 1991.

Merka, V. et al., "Disinfectant properties of some peroxide compounds," Abstract No. 67542e, Chemical Abstracts, vol. 67, p. 6368. Dec. 31, 1967.

MicroPatent Report dated Aug. 18, 2003.

Mulder, R. et al., "Research Note: *Salmonella* Decontamination of Broiler Carcasses with Lactic Acid, L-Cysteine, and Hdrogen Peroxide," Poultry Science, vol. 66, pp. 1555-1557. Dec. 31, 1987.

Nambudripad, V. et al., "Bactericidal Efficiency of Hydrogen Peroxide. Part I. Influence of different concentrations on the rate and extend of destruction of some bacteria of dairy importance," Indian Journal of Dairy Science, vol. 4, pp. 65-69. Dec. 31, 1949.

Opinion Letter dated Apr. 11, 2000.

Orth, R. et al., "Is the control of Listeria, Campylobacter and Yersinia a disinfection problem?," Fleischwirtsch, vol. 69, No. 10, pp. 1575-1576. Dec. 31, 1989.

Parker, W. et al., "Peroxides. IV. Aliphatic Diperacids," Aliphatic Diperacids, vol. 79, pp. 1929-1931. Apr. 20, 1957.

Parker, W. et al. "Peroxides. II. Preparation, Characterization and Polarographic Behavior of Longchain Aliphatic Peracids," Synthesis and Properties of Long Chain Aliphatic Peracids, vol. 77, pp. 4037-4041. Aug. 5, 1955.

Pfizer Chemical Division, "Pfizer Flocon Biopolymers for Industrial Uses (xanthan broths)," Data Sheet 679, pp. 1-4. (year unknown).

Poffe, R. et al., "Disinfection of Effluents from Municipal Sewage Treatment Plants with Peroxy Acids," Zbl. Bakt. Hyg., I. Abt. Orig. B, vol. 167, pp. 337-346. Dec. 31, 1987.

Ranganna, S. et al., "Chemical Preservatives and Anti-oxidants," Indian Food Packer, pp. 30-44. (May-Jun. 1981).

Richardson, B., "On Peroxide of Hydrogen, or Ozone Water, as a Remedy," The Lancet, pp. 707-709, 760-763. Mar. 31, 1891.

Sims, A., "Industrial effluent treatment with hydrogen peroxide," Chemistry and Industry, No. 14, pp. 555-558. Jul. 18, 1983.

Solvay product brochure entitled: Oxymaster-Proxitane Peracetic Acid Applications. (year unknown).

Solvay product brochure entitled: Oxymaster-Proxitane Peracetic Acid Solutions; Handling, Storage and Transport Information (Safety Documentation). (year unknown).

\* cited by examiner

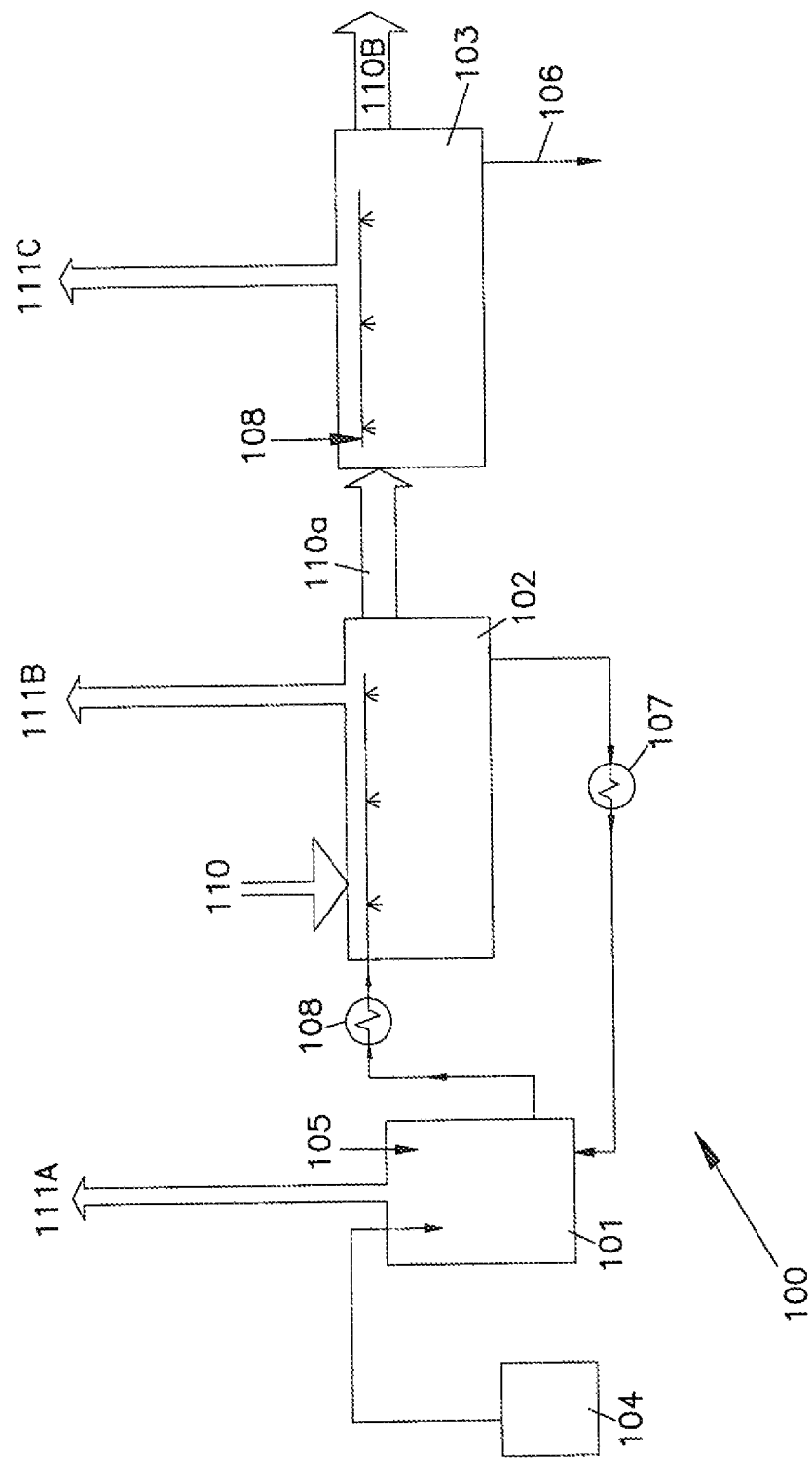

SURFACTANT PEROXYCARBOXYLIC ACID COMPOSITIONS

CROSS REFERENCE TO RELATED APPLICATIONS

This application is a continuation of U.S. patent application Ser. No. 12/792,142 filed Jun. 2, 2010, published as US 2010-0240765, which is a continuation of U.S. patent application Ser. No. 11/176,917 filed Jul. 6, 2005, now U.S. Pat. No. 7,754,670 issued Jul. 13, 2010, the entire disclosures of which are incorporated by reference herein in their entireties.

FIELD OF THE INVENTION

The present invention relates to compositions including surfactant peroxycarboxylic acid, methods for making these compositions, and methods for reducing the population of a microorganism.

BACKGROUND OF THE INVENTION

Conventional peroxycarboxylic acid compositions typically include short chain peroxycarboxylic acids or mixtures of short chain peroxycarboxylic acids and medium chain peroxycarboxylic acids (see, e.g., U.S. Pat. Nos. 5,200,189, 5,314,687, 5,409,713, 5,437,868, 5,489,434, 6,674,538, 6,010,729, 6,111,963, and 6,514,556). Ongoing research efforts have strived for improved peroxycarboxylic acid compositions. In particular, these efforts have strived for compositions that have effective antimicrobial activity, that can be readily made, and that have beneficial properties.

SUMMARY OF THE INVENTION

The present invention relates to compositions including surfactant peroxycarboxylic acid, methods for making these compositions, and methods for reducing the population of a microorganism.

In an embodiment, the present compositions can include surfactant peroxycarboxylic acid and carboxylic acid surfactant plus one or more of acidulant, stabilizing agent, or mixture thereof.

In an embodiment, the present invention includes a method of using a surfactant peroxycarboxylic acid composition. The method can include contacting an object with the present composition (e.g., a use composition) and can result in reducing the population of one or more microorganisms on the object.

BRIEF DESCRIPTION OF THE FIGURE

FIG. 1 is a diagram of a beverage plant, including a cold aseptic filling plant, in which either carbonated or non-carbonated beverages can be prepared and bottled.

DETAILED DESCRIPTION OF THE INVENTION

Definitions

As used herein, the phrase "carboxylic acid surfactant" refers to a surfactant including a carboxylic acid moiety and/or a carboxylate moiety.

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods short chain peroxycarboxylic acid and short chain carboxylic acid; unless such an ingredient is specifically listed after the phrase.

As used herein, the phrase "short chain carboxylic acid" refers to a carboxylic acid that: 1) has characteristic bad, pungent, or acrid odor, and 2) is infinitely soluble in or miscible with water at 20° C. Examples of short chain carboxylic acids include formic acid, acetic acid, propionic acid, and butyric acid.

As used herein, the phrase "short chain peroxycarboxylic acid" refers to the peroxycarboxylic acid form of a short chain carboxylic acid.

As used herein, the phrase "medium chain carboxylic acid" refers to a carboxylic acid that: 1) has reduced or is lacking odor compared to the bad, pungent, or acrid odor associated with an equal concentration of short chain carboxylic acid, and 2) has a critical micellar concentration greater than 1 mM in aqueous buffers at neutral pH. Medium chain carboxylic acids exclude carboxylic acids that are infinitely soluble in or miscible with water at 20° C. Medium chain carboxylic acids include carboxylic acids with boiling points (at 760 mm Hg pressure) of 180 to 300° C. In an embodiment, medium chain carboxylic acids include carboxylic acids with boiling points (at 760 mm Hg pressure) of 200 to 300° C. In an embodiment, medium chain carboxylic acids include those with solubility in water of less than 1 g/L at 25° C. Examples of medium chain carboxylic acids include pentanoic acid, hexanoic acid, heptanoic acid, octanoic acid, nonanoic acid, decanoic acid, undecanoic acid, and dodecanoic acid.

As used herein, the phrase "medium chain peroxycarboxylic acid" refers to the peroxycarboxylic acid form of a medium chain carboxylic acid.

As used herein, a composition or combination "substantially free of" one or more ingredients refers to a composition that includes none of that ingredient or that includes only trace or incidental amounts of that ingredient. Trace or incidental amounts can include the amount of the ingredient found in another ingredient as an impurity or that is generated in a minor side reaction during formation or degradation of the medium chain peroxycarboxylic acid.

As used herein, the phrases "objectionable odor", "offensive odor", or "malodor" refer to a sharp, pungent, or acrid odor or atmospheric environment from which a typical person withdraws if they are able to. Hedonic tone provides a measure of the degree to which an odor is pleasant or unpleasant. An "objectionable odor", "offensive odor", or "malodor" has an hedonic tone rating it as unpleasant as or more unpleasant than a solution of 5 wt-% acetic acid, propionic acid, butyric acid, or mixtures thereof.

As used herein, the term "microorganism" refers to any noncellular or unicellular (including colonial) organism. Microorganisms include all prokaryotes. Microorganisms include bacteria (including cyanobacteria), lichens, fungi, protozoa, virinos, viroids, viruses, phages, and some algae. As used herein, the term "microbe" is synonymous with microorganism.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors. Objects also include the body or part of the body of a living creature, e.g., a hand.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, living eggs, egg products, ready to eat food, wheat, seeds, roots, tubers, leafs, stems, corms, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydro-cooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, "residential" or "institutional" objects or surfaces include those found in structures inhabited by humans. Such objects or surfaces include bathroom surfaces, drains, drain surfaces, kitchen surfaces, and the like.

As used herein, weight percent (wt-%), percent by weight, % by weight, and the like are synonyms that refer to the concentration of a substance as the weight of that substance divided by the weight of the composition and multiplied by 100. Unless otherwise specified, the quantity of an ingredient refers to the quantity of active ingredient.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

Surfactant Peroxycarboxylic Acid Antimicrobial Compositions

The present invention relates to compositions including peroxycarboxylic acids that are also surfactants. The present invention includes surfactant peroxycarboxylic acid compositions. The present surfactant peroxycarboxylic acid compositions can include a carrier. In an embodiment, the present compositions include surfactant peroxycarboxylic acid, carboxylic acid surfactant, and carrier. Unexpectedly, in certain embodiments, the present surfactant peroxycarboxylic acid compositions can exhibit effective antimicrobial activity against one or more of a variety of microbes. For example, the peroxycarboxylic acid surfactant compositions can exhibit antimicrobial activity against both gram negative and gram positive bacteria. Unexpectedly, the present surfactant carboxylic acids can be generated from a mixture of oxidizing agent and carboxylic acid surfactant. For example, the peroxycarboxylic acid surfactant compositions can be generated at a level producing concentrate compositions that can be diluted to form effective antimicrobial use compositions.

In certain embodiments, the present composition can include at least one of oxidizing agent, acidulant, stabilizing agent, mixtures thereof, or the like. The present composition can include any of a variety of oxidizing agents, for example, hydrogen peroxide. The oxidizing agent can be effective to convert a carboxylic acid surfactant to a surfactant peroxycarboxylic acid. The oxidizing agent can also have antimicrobial activity, although it may not be present at a concentration sufficient to exhibit such activity. The present composition can include any of a variety of acidulants, for example, an inorganic acid. The acidulant can be effective to bring the pH of the present concentrate composition to less than 1, or to bring the pH of the present use composition to about 5 or below, about 4 or below, or about 3 or below. The acidulant can augment the antimicrobial activity of the present composition. The present composition can include any of a variety of stabilizing agents, for example, sequestrant, for example, phosphonate sequestrant. The sequestrant can be effective to stabilize the surfactant peroxycarboxylic acid.

Compositions of Surfactant Peroxycarboxylic Acid and/or Carboxylic Acid Surfactant As used herein, the phrase, "surfactant peroxycarboxylic acid" refers to the peroxycarboxylic acid form of a carboxylic acid surfactant. The composition or method of the present invention can include one or more surfactant peroxycarboxylic acids and, optionally, one or more carboxylic acid surfactants. Suitable peroxycarboxylic acids include the peroxycarboxylic acid form of a carboxylic acid surfactant that is an anionic surfactant, an amphoteric surfactant, and/or a zwitterionic surfactant. Examples of suitable anionic surfactants, amphoteric surfactants, and zwitterionic surfactants that, in their peroxycarboxylic acid form, can serve as surfactant peroxycarboxylic acids in the present invention are described hereinbelow.

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted.

Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide. In an embodiment, the peroxycarboxylic acid can be made by the direct, acid catalyzed equilibrium action of hydrogen peroxide on the carboxylic acid surfactant. Scheme 1 illustrates an equilibrium between carboxylic acid and oxidizing agent (Ox) on one side and peroxycarboxylic acid and reduced oxidizing agent ($Ox_{red}$) on the other:

$$RCOOH + Ox \leftrightarrows RCOOOH + Ox_{red} \qquad (1)$$

Scheme 2 illustrates an embodiment of the equilibrium of scheme 1 in which the oxidizing agent is hydrogen peroxide on one side and peroxycarboxylic acid and water on the other:

$$RCOOH + H_2O_2 \leftrightarrows RCOOOH + H_2O \qquad (2)$$

Although not limiting to the present invention, it is believed that the present compositions have an equilibrium constant of about greater than about 1000.

The composition and methods of the invention can employ surfactant peroxycarboxylic acids containing, for example, at least one alkyl amine moiety, at least one alkyl carboxylate moiety, at least one alkyl amide moiety, at least one sulfonate moiety, and/or at least one alkoxylate moiety.

Suitable surfactant peroxycarboxylic acids include those described by Formula A: $(R_1)(R_2)X(R_3COOOH)$. In certain embodiments, in Formula A, $R_1$ and $R_2$ can independently be absent, alkyl moiety, alkyl carboxylate moiety, alkyl amide moiety, alkyl sulfonate moiety, or alkoxylate moiety; X can be N, NH, C=O, or CH2; and $R_3$ can be alkyl or alkyl sulfonate moiety.

In certain embodiments, suitable surfactant peroxycarboxylic acids include those described by Formula B: $(R_1)(R_2)N(R_3COOOH)$. In Formula B, for example, $R_1$ and $R_2$ can independently be alkyl moiety, alkyl carboxylate moiety, alkyl amide moiety, alkyl sulfonate moiety, or alkoxylate moiety and $R_3$ can be alkyl or alkyl sulfonate moiety.

In certain embodiments, suitable surfactant peroxycarboxylic acids include those described by Formula C: $(R_1)C(O)(R_3COOOH)$. In Formula C, for example, $R_1$ can be alkoxylate moiety and $R_3$ can be alkyl or alkyl sulfonate moiety.

In certain embodiments, suitable surfactant peroxycarboxylic acids include those described by Formula D: $(R_1)CH_2(R_3COOOH)$. In Formula D, for example, $R_1$ can be alkoxylate moiety and $R_3$ can be absent, alkyl, or alkyl sulfonate moiety.

Suitable alkyl moieties include C1 to C16 alkyl moieties, straight chain or branched. Suitable C1 to C16 alkyl moieties include C6 to C14 alkyl moieties, for example, C8, C11, C12, or C13 alkyl moieties. Suitable C1 to C16 alkyl moieties include C1 to C6 alkyl moieties, for example, C2 or C3 straight chain alkyl moieties.

Suitable alkyl carboxylate moieties include C1 to C6 alkyl carboxylate moieties, straight chain or branched. Suitable alkyl components of the alkyl carboxylate moieties include those described hereinabove. Suitable alkyl carboxylate moieties include those described by the formula $-(CH_2)_{1-6}COOH$, e.g., $-(CH_2)_2COOH$, or salts thereof.

Suitable alkyl amide moieties include C1 to C6 alkyl amide moieties, straight chain or branched, with substituted or unsubstituted nitrogen. Suitable alkyl components of the alkyl amides include those described hereinabove. Suitable alkyl amide moieties include those described by the formula $-(CH_2)_{1-6}CONHR$, e.g., $-(CH_2)_2CONHR$.

Suitable alkyl sulfonate moieties include C1 to C6 alkyl sulfonate moieties, straight chain or branched, which can also include a carboxyl group. Suitable alkyl components of the alkyl sulfonate moieties include those described hereinabove. Suitable alkyl sulfonate moieties include those described by the formula $-(CH_2)_{0-6}-(CHSO_3H)-(CH_2)_{1-6}COOH$, e.g., $-CH(SO3H)CH_2COOH$.

Suitable alkoxylate moieties include moieties such as ethoxylate or propoxylate moieties. Suitable alkoxylate moieties can be described by Formula E: $R_4O((CH_2)_{2-3}O)_n-$. In certain embodiments, in Formula E, $R_4$ can be alkyl, such as C8 to C24 alkyl, e.g., C10 to C14 alkyl, C11 alkyl, C12 alkyl, or C13 alkyl; n can be about 1 to about 12 or about 1 to about 6, e.g., about 2 to about 4 or about 3; and/or $(CH_2)_{2-3}$ can be $(CH_2)_2$.

Peroxycarboxylic acids useful in the compositions and methods of the present invention surfactant peroxycarboxylic acids described by Formulas F-I:

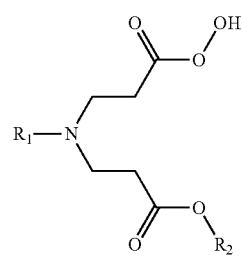

Formula F

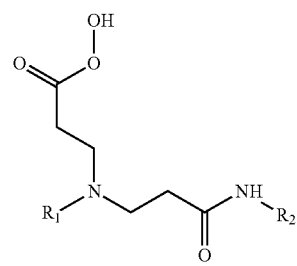

Formula G

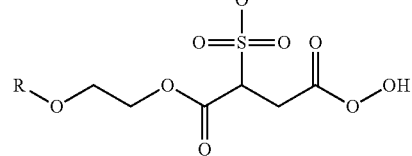

Formula H

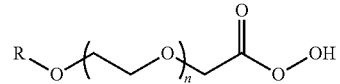

Formula I

In Formula F, $R_1$ can be $C_8H_{17}$ and $R_2$ can be H or OH. The nitrogen can be protonated or unprotonated. In Formula G, $R_1$ and $R_2$ can be $C_8H_{17}$. The nitrogen can be protonated or unprotonated. In Formula H, R can be $C_{11}H_{23}$ and the sulfonate can be in the form of a sodium salt. In Formula I, R can be $C_{12}H_{25}$, $C_{13}H_{27}$, or a mixture thereof; and n can be 3. Each of Formulas F-I also includes the deprotonated form in which the RCOOOH group is present as $RCOOO^-$.

The composition of the present invention can include a carboxylic acid. Generally, carboxylic acids have the formula R—COOH wherein the R can represent any number of different groups including alkyl, arylalkyl, cycloalkyl, aromatic, or heterocyclic groups, all of which can be saturated or unsaturated as well as substituted or unsubstituted. Carboxylic acids can have one, two, three, or more carboxyl groups. Suitable carboxylic acids include carboxylic acid surfactants. Suitable carboxylic acid surfactants include those categorized as an anionic surfactant, an amphoteric surfactant, and/or a zwitterionic surfactant. Examples of suitable anionic surfactants, amphoteric surfactants, and zwitterionic surfactants are described hereinbelow.

The composition and methods of the invention can employ carboxylic acid surfactant containing, for example, at least one alkyl amine moiety, at least one alkyl carboxylate moiety, at least one alkyl amide moiety, at least one sulfonate moiety, and/or at least one alkoxylate moiety. In an embodiment, the compositions and methods include a surfactant peroxycarboxylic acid and the corresponding carboxylic acid surfactant.

Suitable carboxylic acid surfactants include those described by Formula J: $(R_1)(R_2)X(R_3COOH)$. In certain embodiments, in Formula J, $R_1$ and $R_2$ can independently be absent, alkyl moiety, alkyl carboxylate moiety, alkyl amide moiety, alkyl sulfonate moiety, or alkoxylate moiety; X can be N, NH, C=O, or CH2; and $R_3$ can be alkyl or alkyl sulfonate moiety.

In certain embodiments, suitable carboxylic acid surfactants include those described by Formula K: $(R_1)(R_2)N(R_3COOH)$. In Formula K, for example, $R_1$ and $R_2$ can independently be alkyl moiety, alkyl carboxylate moiety, alkyl amide moiety, alkyl sulfonate moiety, or alkoxylate moiety and $R_3$ can be alkyl or alkyl sulfonate moiety.

In certain embodiments, suitable carboxylic acid surfactants include those described by Formula L: $(R_1)C(O)(R_3COOH)$. In Formula L, for example, $R_1$ can be alkoxylate moiety and $R_3$ can be alkyl or alkyl sulfonate moiety.

In certain embodiments, suitable carboxylic acid surfactants include those described by Formula M: $(R_1)CH_2(R_3COOH)$. In Formula M, for example, $R_1$ can be alkoxylate moiety and $R_3$ can be absent, alkyl, or alkyl sulfonate moiety.

Carboxylic acids useful in the compositions and methods of the present invention carboxylic acid surfactants described by Formulas N-Q:

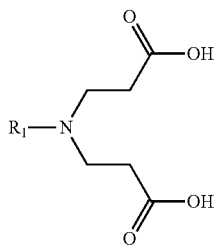

Formula N

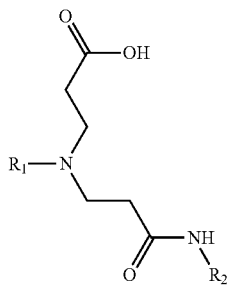

Formula O

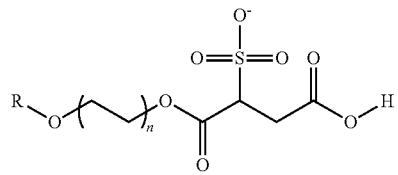

Formula P

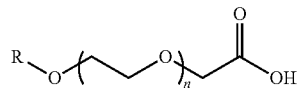

Formula Q

In Formula N, $R_1$ can be $C_8H_{17}$ and the nitrogen can be protonated or unprotonated. In Formula O, $R_1$ and $R_2$ can be $C_8H_{17}$. The nitrogen can be protonated or unprotonated. In Formula P, R can be $C_{11}H_{23}$ and the sulfonate can be in the form of a sodium salt. In Formula I, Q can be $C_{12}H_{25}$, $C_{13}H_{27}$, or a mixture thereof; and n can be 3. Each of Formulas N-Q also includes the deprotonated form in which the carboxyl group is present as a carboxylate or a salt thereof.

Suitable carboxylic acid surfactants include octyliminodiproprionate (sold under the tradenames Mackam ODP, 50% active, and Mirataine JC HA, 42% active), laurethsulfonsuccinate (e.g., the disodium salt) (sold under the tradename Makanate EL. 39% active), linear alcohol ethoxycarboxylate (sold under the tradename Neodox 23-4), mixtures thereof, or the like; and their corresponding surfactant peroxycarboxylic acids.

In certain embodiments, the present composition includes about 0.5 to about 15 wt-% surfactant peroxycarboxylic acid, about 1 to about 10 wt-% surfactant peroxycarboxylic acid, about 2 to about 6 wt-% surfactant peroxycarboxylic acid, or about 3 to about 4 wt-% surfactant peroxycarboxylic acid. The composition can include any of these ranges or amounts not modified by about.

In certain embodiments, the present composition includes about 0.5 to about 20 wt-% carboxylic acid surfactant, about 1 to about 15 wt-% carboxylic acid surfactant, or about 1 to about 6 wt-% carboxylic acid surfactant. The composition can include any of these ranges or amounts not modified by about.

In certain embodiments, the present composition includes surfactant peroxycarboxylic acid that can be stable for a reasonably expected shelf life of a product. For example, in an embodiment, the surfactant peroxycarboxylic acid can be stable for about 1 year. For example, in an embodiment, the surfactant peroxycarboxylic acid can be stable for at least about 1 year.

In an embodiment, the present composition includes an amount of surfactant peroxycarboxylic acid effective for killing one or more of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold, and the like. In an embodiment, the present composition includes an amount of surfactant peroxycarboxylic acid effective for killing one or more of the pathogenic bacteria associated with a health care surfaces and environments, such as *Salmonella typhimurium, Staphylococcus aureus, Salmonella choleraesurus, Pseudomonas aeruginosa, Escherichia coli*, mycobacteria, yeast, mold, and the like. The compositions and methods of the present invention have activity against a wide variety of microorganisms such as Gram positive (for example, *Listeria monocytogenes* or *Staphylococcus aureus*) and Gram negative (for example, *Escherichia coli* or

*Pseudomonas aeruginosa*) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

Embodiments of the present invention include carboxylic acid surfactant and surfactant peroxycarboxylic acid, and certain embodiments specifically exclude short chain peroxycarboxylic acid, short chain carboxylic acid, or mixture thereof. Nonetheless embodiments of the present compositions can include short chain peroxycarboxylic acid, short chain carboxylic acid, or mixture thereof. It is not intended that addition of short chain peroxycarboxylic acid, short chain carboxylic acid, or mixture thereof to a composition should necessarily take a composition outside the spirit and scope of the present invention.

Anionic Surfactants

Suitable surfactant peroxycarboxylic acids include peroxycarboxylic acid forms of anionic surfactant. Suitable anionic surfactants include any anionic surfactant including a carboxyl or carboxylate moiety, e.g., a carboxylate surfactant. In an embodiment, the anionic surfactant includes alcohol alkoxylate carboxylate, sarcosinate, taurate, acyl amino acid, alkanoic ester, salt or acid form thereof, or mixture thereof. The particular salts will be suitably selected depending upon the particular formulation and the needs therein. Suitable salts include ammonium and substituted ammonium (such as mono-, di- and triethanolamine) and alkali metal (such as sodium, lithium and potassium) salts, mixtures thereof, or the like.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. In an embodiment, the secondary carboxylate surfactants contain no ether linkages, no ester linkages, and/or no hydroxyl groups. Further, they can lack nitrogen atoms in the head-group (amphiphilic portion). Suitable secondary soap surfactants can contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of Formula R:

R—O—(CH$_2$CH$_2$O)$_n$(CH$_2$)$_m$—CO$_2$X in which R is a C$_8$ to C$_{22}$ alkyl group or

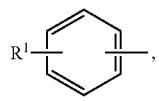

in which R$^1$ is a C$_4$-C$_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In an embodiment, in Formula R, n is an integer of 4 to 10 and m is 1. In an embodiment, in Formula R, R is a C$_8$-C$_{16}$ alkyl group. In an embodiment, in Formula R, R is a C$_{12}$-C$_{14}$ alkyl group, n is 4, and m is 1.

In an embodiment, in Formula R, R is

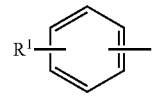

and R$^1$ is a C$_6$-C$_{12}$ alkyl group. In an embodiment, in Formula R, R$^1$ is a C$_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a C$_{12-13}$ alkyl polyethoxy (4) carboxylic acid (Shell Chemical), and Emcol CNP-110, a C$_9$ alkylaryl polyethoxy (10) carboxylic acid (Witco Chemical). Carboxylates are also available from Clariant, e.g. the product Sandopan® DTC, a C$_{13}$ alkyl polyethoxy (7) carboxylic acid.

Suitable anionic surfactants include octyliminodipropionate (sold under the tradenames Mackam ODP, 50% active, and Mirataine JC HA, 42% active), laurethsulfonsuccinate (e.g., the disodium salt) (sold under the tradename Makanate EL. 39% active), linear alcohol ethoxycarboxylate (sold under the tradename Neodox 23-4), mixtures thereof, or the like; and their corresponding surfactant peroxycarboxylic acids.

Amphoteric Surfactants

Amphoteric, or ampholytic, surfactants contain both a basic and an acidic hydrophilic group and an organic hydrophobic group. These ionic entities may be any of a variety anionic or cationic groups employed in surfactants. In an embodiment, the amphoteric surfactant includes a basic nitrogen and an acidic carboxylate group as the basic and acidic hydrophilic groups, respectively.

Amphoteric surfactants can be broadly described as derivatives of aliphatic secondary and tertiary amines, in which the aliphatic radical can be straight chain or branched and wherein one of the aliphatic substituents can contain from about 8 to 18 carbon atoms and one contains an anionic water solubilizing group, e.g., carboxyl group. Amphoteric surfactants can be subdivided into two major known classes, such as described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by any of a variety of known methods. For example, 2-alkyl hydroxyethyl imidazoline can be synthesized by condensation and ring closure of a long chain carboxylic acid (or a derivative) with dialkyl ethylenediamine. Commercial amphoteric surfactants can be derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazoline derivatives having application in the present invention generally have the general formula:

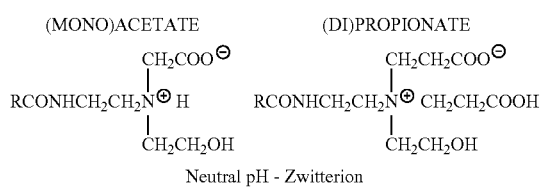

Neutral pH - Zwitterion wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled Zwitterionic Surfactants.

Long chain N-alkylamino acids can be readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$, and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+(CH_2$—$CH_2$—$CO_2Na)_2$—$CH_2$—$CH_2$—OH or $C_{12}$-alkyl-C(O)—N(H)—$CH_2$—$CH_2$—$N^+(CH_2$—$CO_2Na)_2$—$CH_2$—$CH_2$—OH.

Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J. Another suitable amphoteric surfactant includes octyliminodipropionate, which is sold under the tradename Mackam ODP.

Suitable amphoteric surfactants include octyliminodipropionate (sold under the tradenames Mackam ODP, 50% active, and Mirataine JC HA, 42% active), laurethsulfonsuccinate (e.g., the disodium salt) (sold under the tradename Makanate EL. 39% active), mixtures thereof, or the like; and their corresponding surfactant peroxycarboxylic acids.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. In an embodiment, a zwitterionic surfactant includes a positive charged quaternary ammonium or, in some cases, a sulfonium or phosphonium ion; a negative charged carboxyl group; and an alkyl group. Zwitterionics can contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxyl group. Suitable zwitterionic surfactants include betaine and sultaine surfactants.

A general formula for these compounds is:

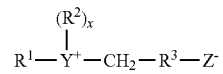

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y can be nitrogen, phosphorus, or sulfur atom; $R^2$ can be an alkyl or monohydroxy alkyl group containing 1 to 3 carbon atoms; x is 1 when Y is a sulfur atom and 2 when Y is a nitrogen or phosphorus atom; $R^3$ can be an alkylene or hydroxy alkylene or hydroxy alkylene of from 1 to 4 carbon atoms; and Z is a carboxylate.

Examples of zwitterionic surfactants having the structures listed above include: 4-[N,N-di(2-hydroxyethyl)-N-octadecylammonio]-butane-1-carboxylate and 4-[N,N-di(2(2-hydroxyethyl)-N(2-hydroxydodecyl)ammonio]-butane-1-carboxylate. The alkyl groups contained in said detergent surfactants can be straight or branched and saturated or unsaturated.

A listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Embodiments of Compositions

Some examples of representative constituent concentrations for embodiments of the present compositions can be found in Tables A and B, in which the values are given in wt-% of the ingredients in reference to the total composition weight. In certain embodiments, the proportions and amounts in Tables A and B can be modified by "about".

TABLE A

| Ingredient | wt-% | wt-% | wt-% | wt-% |
|---|---|---|---|---|
| surfactant peroxycarboxylic acid | 0.5-20 | 3-15 | 6-12 | 8-10 |
| carboxylic acid surfactant | 0.5-20 | 0.5-20 | 1-10 | 1-6 |
| carrier | 5-90 | 10-80 | 15-50 | 25-35 |

TABLE B

| Ingredient | wt-% | wt-% | wt-% | wt-% |
|---|---|---|---|---|
| surfactant peroxycarboxylic acid | 0.5-20 | 3-15 | 6-12 | 8-10 |
| carboxylic acid surfactant | 0.5-20 | 0.5-20 | 1-10 | 1-6 |
| carrier | 5-90 | 10-80 | 15-50 | 25-35 |
| oxidizing agent | 2-50 | 5-40 | 5-30 | 10-20 |
| acidulant | 10-80 | 20-70 | 30-70 | 35-65 |
| stabilizing agent | 0.2-10 | 0.4-4 | 0.6-3 | 1-2 |

In certain embodiments, the present composition includes about 0.5 to about 15 wt-% surfactant peroxycarboxylic acid, about 1 to about 10 wt-% surfactant peroxycarboxylic acid, about 2 to about 6 wt-% surfactant peroxycarboxylic acid, or about 3 to about 4 wt-% surfactant peroxycarboxylic acid. The composition can include any of these ranges or amounts not modified by about.

In certain embodiments, the present composition includes about 0.5 to about 20 wt-% carboxylic acid surfactant, about 1 to about 15 wt-% carboxylic acid surfactant, or about 1 to about 6 wt-% carboxylic acid surfactant. The composition can include any of these ranges or amounts not modified by about.

In certain embodiments, the present composition includes about 5 to about 90 wt-% carrier, about 10 to about 80 wt-% carrier, about 20 to about 40 wt-% carrier, or about 25 to about 35 wt-% carrier. The composition can include any of these ranges or amounts not modified by about.

In certain embodiments, the present composition includes about 2 to about 50 wt-% oxidizing agent, about 5 to about 40 wt-% oxidizing agent, about 5 to about 30 wt-% oxidizing agent, or about 10 to about 20 wt-% oxidizing agent. The composition can include any of these ranges or amounts not modified by about.

In certain embodiments, the present composition includes about 10 to about 80 wt-% acidulant, about 20 to about 70 wt-% acidulant, about 30 to about 70 wt-% acidulant, or about 35 to about 65 wt-% acidulant. The composition can include any of these ranges or amounts not modified by about.

In certain embodiments, the present composition includes about 0.2 to about 10 wt-% stabilizing agent, about 0.4 to about 4 wt-% stabilizing agent, about 0.6 to about 3 wt-% stabilizing agent, or about 1 to about 2 wt-% stabilizing agent. The composition can include any of these ranges or amounts not modified by about.

In certain embodiments, the present composition includes about 0.5 to about 15 wt-% surfactant peroxycarboxylic acid, about 0.5 to about 20 wt-% carboxylic acid surfactant, and/or about 5 to about 90 wt-% carrier. In certain embodiments, the present composition includes about 1 to about 10 wt-% surfactant peroxycarboxylic acid, about 0.5 to about 20 wt-% carboxylic acid surfactant, and/or about 10 to about 80 wt-% carrier. In certain embodiments, the present composition includes about 2 to about 6 wt-% surfactant peroxycarboxylic acid, about 1 to about 15 wt-% carboxylic acid surfactant, and/or about 20 to about 40 wt-% carrier. In certain embodiments, about 3 to about 4 wt-% surfactant peroxycarboxylic acid, about 1 to about 6 wt-% carboxylic acid surfactant, and/or about 25 to about 35 wt-% carrier. The composition can include any of these ranges or amounts not modified by about.

In certain embodiments, the present composition includes about 0.5 to about 15 wt-% surfactant peroxycarboxylic acid, about 0.5 to about 20 wt-% carboxylic acid surfactant, about 5 to about 90 wt-% carrier, about 2 to about 50 wt-% oxidizing agent, about 10 to about 80 wt-% acidulant, and/or about 0.2 to about 10 wt-% stabilizing agent. The composition can include any of these ranges or amounts not modified by about.

In certain embodiments, the present composition includes about 1 to about 10 wt-% surfactant peroxycarboxylic acid, about 0.5 to about 20 wt-% carboxylic acid surfactant, about 10 to about 80 wt-% carrier, about 5 to about 40 wt-% oxidizing agent, about 20 to about 70 wt-% acidulant, and/or about 0.4 to about 4 wt-% stabilizing agent. The composition can include any of these ranges or amounts not modified by about.

In certain embodiments, the present composition includes about 2 to about 6 wt-% surfactant peroxycarboxylic acid, about 1 to about 15 wt-% carboxylic acid surfactant, about 20 to about 40 wt-% carrier, about 5 to about 30 wt-% oxidizing agent, about 30 to about 70 wt-% acidulant, and/or about 0.6 to about 3 wt-% stabilizing agent. The composition can include any of these ranges or amounts not modified by about.

In certain embodiments, about 3 to about 4 wt-% surfactant peroxycarboxylic acid, about 1 to about 6 wt-% carboxylic acid surfactant, about 25 to about 35 wt-% carrier, about 10 to about 20 wt-% oxidizing agent, about 35 to about 65 wt-% acidulant, about 1 to about 2 wt-% stabilizing agent. The composition can include any of these ranges or amounts not modified by about.

In an embodiment, the compositions of the present invention include only ingredients that can be employed in food products or in food wash, handling, or processing, for example, according to government (e.g. FDA or USDA) rules and regulations, 21 CFR §170-178. In an embodiment, the compositions of the present invention can include only ingredients at the concentrations approved for incidental food contact by the USEPA, 40 CFR §180.940.

The present compositions can take the form of a liquid, solid, gel, paste, unit dose, gel pack, or the like. The present compositions can be supplied in any of a variety of containers or media, such as in a 2 compartment dispenser or as a pre-moistened wipe, towelette, or sponge.

Compositions Including Medium Chain Carboxylic Acid and/or Peroxycarboxylic Acid The composition and methods of the invention can also include medium chain peroxycarboxylic acids containing, for example, 6 to 12 carbon atoms. For example, medium chain peroxycarboxylic (or percarboxylic) acids can have the formula $R(CO_3H)_n$, where R is a $C_5$-$C_{11}$ alkyl group, a $C_5$-$C_{11}$ cycloalkyl, a $C_5$-$C_{11}$ arylalkyl group, $C_5$-$C_{11}$ aryl group, or a $C_5$-$C_{11}$ heterocyclic group; and n is one, two, or three. Medium chain peroxycarboxylic acids useful in the compositions and methods of the present invention include peroxypentanoic, peroxyhexanoic, peroxyheptanoic, peroxyoctanoic, peroxynonanoic, peroxydecanoic, peroxyundecanoic, peroxydodecanoic, peroxyascorbic, peroxyadipic, peroxycitric, peroxypimelic, or peroxysuberic acid, mixtures thereof, or the like. The alkyl backbones of these medium chain peroxycarboxylic acids can be straight chain, branched, or a mixture thereof. Peroxy forms of carboxylic acids with more than one carboxylate moiety can have one or more of the carboxyl moieties present as peroxycarboxyl moieties.

Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid is surface active and can assist in wetting hydrophobic surfaces, such as those of microbes.

The medium chain peroxycarboxylic acid can include or be a C6 to C12 peroxycarboxylic acid. The C6 to C12 peroxycarboxylic acid can include or be peroxyhexanoic acid, peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C7 to C12 peroxycarboxylic acid. The C7 to C12 peroxycarboxylic acid can include or be peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C6 to C10 peroxycarboxylic acid. The C6 to C10 peroxycarboxylic acid can include or be peroxyhexanoic acid, peroxyheptanoic acid, peroxyoctanoic acid, peroxynonanoic acid, peroxydecanoic acid, or mixture thereof. The medium chain peroxycarboxylic acid can include or be a C8 to C10 peroxycarboxylic acid. The C8 to C10 peroxycarboxylic acid can include or be peroxyoctanoic acid, peroxynonanoic acid, peroxydecanoic acid, or mixture thereof. In certain embodiments, the medium chain peroxyoctanoic acid includes or is peroxyoctanoic acid, peroxydecanoic acid, or mixture thereof. In an embodiment, the medium chain peroxycarboxylic acid includes or is peroxyoctanoic acid.

In certain embodiments, the present composition includes about 0.0005 to about 5 wt-% medium chain peroxycarboxylic acid, about 0.3 to about 7 wt-% medium chain peroxycarboxylic acid, about 0.5 to about 5 wt-% medium chain peroxycarboxylic acid, about 0.5 to about 4 wt-% medium chain peroxycarboxylic acid, about 0.8 to about 3 wt-% medium chain peroxycarboxylic acid, about 1 to about 3 wt-% medium chain peroxycarboxylic acid, or about 1 to about 2 wt-% medium chain peroxycarboxylic acid. The composition can include any of these ranges or amounts not modified by about.

The composition and methods of the invention can include medium chain carboxylic acids containing, for example, 6 to 12 carbon atoms. For example, medium chain carboxylic acids can have the formula R—COOH in which R can be a $C_5$-$C_{11}$ alkyl group, a $C_5$-$C_{11}$ cycloalkyl group, a $C_5$-$C_{11}$ arylalkyl group, $C_5$-$C_{11}$ aryl group, or a $C_5$-$C_{11}$ heterocyclic group. Suitable medium chain carboxylic acids include pentanoic, hexanoic, heptanoic, octanoic, nonanoic, decanoic, undecanoic, dodecanoic, ascorbic, citric, adipic, pimelic, and suberic acid. The alkyl backbones of these medium chain carboxylic acids can be straight chain, branched, or a mixture thereof. Carboxylic acids which are generally useful are those having one or two carboxyl groups where the R group is a primary alkyl chain having a length of $C_4$ to $C_{11}$. The primary alkyl chain is that carbon chain of the molecule having the greatest length of carbon atoms and directly appending carboxyl functional groups.

In an embodiment, the present compositions and methods include a medium chain carboxylic acid. The medium chain carboxylic acid can include or be a C6 to C12 carboxylic acid. The C6 to C12 carboxylic acid can include or be hexanoic acid, heptanoic acid, octanoic acid, nonanoic acid, decanoic acid, undecanoic acid, dodecanoic acid, or mixture thereof. The medium chain carboxylic acid can include or be a C7 to C12 carboxylic acid. The C7 to C12 carboxylic acid can include or be heptanoic acid, octanoic acid, nonanoic acid, decanoic acid, undecanoic acid, dodecanoic acid, or mixture thereof. The medium chain peroxycarboxylic acid can include or be a C6 to C10 carboxylic acid. The C6 to C10 carboxylic acid can include or be hexanoic acid, heptanoic acid, octanoic acid, nonanoic acid, decanoic acid, or mixture thereof. The medium chain carboxylic acid can include or be a C8 to C10 carboxylic acid. The C8 to C10 carboxylic acid can include or be octanoic acid, nonanoic acid, decanoic acid, or mixture thereof. In certain embodiments, the medium chain carboxylic acid includes or is octanoic acid, decanoic acid, or mixture thereof. In an embodiment, the medium chain carboxylic acid includes or is octanoic acid.

In certain embodiments, the present composition includes about 0.001 to about 8 wt-% medium chain carboxylic acid, about 1 to about 10 wt-% medium chain carboxylic acid, about 1 to about 8 wt-% medium chain carboxylic acid, about 1.5 to about 6 wt-% medium chain carboxylic acid, about 2 to about 8 wt-% medium chain carboxylic acid, about 2 to about 6 wt-% medium chain carboxylic acid, about 2 to about 4 wt-% medium chain carboxylic acid, about 2.5 to about 5 wt-% medium chain carboxylic acid, about 3 to about 6 wt-% medium chain carboxylic acid, or about 3 to about 5 wt-% medium chain carboxylic acid. The composition can include any of these ranges or amounts not modified by about.

In an embodiment, the compositions and methods include a medium chain peroxycarboxylic acid and the corresponding medium chain carboxylic acid.

In an embodiment, the present composition includes an amount of medium chain peroxycarboxylic acid effective for killing one or more of the food-borne pathogenic bacteria associated with a food product, such as *Salmonella typhimurium, Salmonella javiana, Campylobacter jejuni, Listeria monocytogenes,* and *Escherichia coli* O157:H7, yeast, mold, and the like. In an embodiment, the present composition includes an amount of medium chain peroxycarboxylic acid effective for killing one or more of the pathogenic bacteria associated with a health care surfaces and environments, such as *Salmonella typhimurium, Staphylococcus aureus, Salmonella choleraesurus, Pseudomonas aeruginosa, Escherichia coli*, mycobacteria, yeast, mold, and the like. The compositions and methods of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

In an embodiment, the present composition need not include substantial amounts of short chain peroxycarboxylic acid. For example, the present compositions can be free of added short chain peroxycarboxylic acid. As used herein, free of added material refers to a composition that includes the material only as a incidental or trace quantity found, for example, as an ingredient of or impurity in another named ingredient or incidentally generated from a minor side reaction.

In an embodiment, the present composition includes medium chain peroxycarboxylic acid and only relatively small amounts of short chain peroxycarboxylic acid. For example, the present composition can include about 1 or more parts of medium chain peroxycarboxylic acid for each 8 parts of short chain carboxylic acid, short chain peroxycarboxylic acid, or mixture thereof. For example, the present composition can include short chain peroxycarboxylic acid at a level insufficient to cause odor offensive to a typical person.

In certain embodiments, the present composition includes medium chain peroxycarboxylic acid and does not include substantial amounts of peroxyacetic acid, is free of added peroxyacetic acid, includes about 1 or more parts of medium chain peroxycarboxylic acid for each 8 parts of peroxyacetic acid, or includes peroxyacetic acid at a level insufficient to cause odor offensive to a typical person.

In an embodiment, the present composition includes medium chain peroxycarboxylic acid and need not include substantial amounts of short chain carboxylic acid. For example, the present compositions can be free of added short chain carboxylic acid. In an embodiment, the present composition includes only relatively small amounts of short chain carboxylic acid. By way of further example, the present composition can include about 1 or more parts of medium chain peroxycarboxylic acid for each 8 parts of short chain carboxylic acid. For example, the present composition can include short chain carboxylic acid at a level insufficient to cause odor offensive to a typical person.

In certain embodiments, the present composition includes medium chain peroxycarboxylic acid and does not include substantial amounts of acetic acid, is free of added acetic acid, includes about 1 or more parts of medium chain peroxycarboxylic acid for each 8 parts of acetic acid, or includes acetic acid at a level insufficient to cause odor offensive to a typical person. In certain embodiments, the present compositions include, for example, less than 10 wt-%, less than less than 5 wt-%, less than 2 wt-%, or less than 1 wt-% acetic acid. In certain embodiments, the present use compositions include, for example, less than 40 ppm, less than 20 ppm, less than 10 ppm, or less than 5 ppm acetic acid.

In an embodiment, the present composition includes medium chain peroxycarboxylic acid and need not include substantial amounts of short chain peroxycarboxylic acid, short chain carboxylic acid, or mixture thereof. For example, the present compositions can be free of added short chain peroxycarboxylic acid, short chain carboxylic acid, or mixture thereof. For example, the present composition can include short chain carboxylic acid, short chain peroxycarboxylic acid, or mixture thereof at a level insufficient to cause odor offensive to a typical person. In certain embodiments, the present composition does not include substantial amounts of acetic acid, peroxyacetic acid, or mixtures thereof; is free of added acetic acid, peroxyacetic acid, or mixtures thereof; includes about 1 or more parts of medium chain peroxycarboxylic acid for each 8 parts of acetic acid, peroxyacetic acid, or mixtures thereof; or includes acetic acid, peroxyacetic acid, or mixtures thereof at a level insufficient to cause odor offensive to a typical person.

In an embodiment, the present composition includes about 1 or more parts of medium chain peroxycarboxylic acid for each 8 parts of short chain carboxylic acid, short chain peroxycarboxylic acid, or mixture thereof. In an embodiment, the present composition includes about 1 or more parts of medium chain peroxycarboxylic acid for each 7 parts of short chain carboxylic acid, short chain peroxycarboxylic acid, or mixture thereof. In an embodiment, the present composition includes about 1 or more parts of medium chain peroxycarboxylic acid for each 6 parts of short chain carboxylic acid, short chain peroxycarboxylic acid, or mixture thereof. In an embodiment, the present composition includes about 1 or more parts of medium chain peroxycarboxylic acid for each 5 parts of short chain carboxylic acid, short chain peroxycarboxylic acid, or mixture thereof. In an embodiment, the present composition includes about 1 or more parts of medium chain peroxycarboxylic acid for each 4 parts of short chain carboxylic acid, short chain peroxycarboxylic acid, or mixture thereof. In an embodiment, the present composition includes about 1 or more parts of medium chain peroxycarboxylic acid for each 3 parts of short chain carboxylic acid, short chain peroxycarboxylic acid, or mixture thereof. In an embodiment, the present composition includes about 1 or more parts of medium chain peroxycarboxylic acid for each 2 parts of short chain carboxylic acid, short chain peroxycarboxylic acid, or mixture thereof. In an embodiment, the present composition includes about 1 or more parts of medium chain peroxycarboxylic acid for each 1 part of short chain carboxylic acid, short chain peroxycarboxylic acid, or mixture thereof.

In an embodiment, the present composition has an odor less unpleasant than (e.g., as measured by an hedonic tone rating) than 5, 4, 3, 2, or 1 wt-% acetic acid in water. In an embodiment, the present composition has an odor less unpleasant than (e.g., as measured by an hedonic tone rating) than 5 wt-% acetic acid in water. In an embodiment, the present composition has an odor less unpleasant than (e.g., as measured by an hedonic tone rating) than 4 wt-% acetic acid in water. In an embodiment, the present composition has an odor less unpleasant than (e.g., as measured by an hedonic tone rating) than 3 wt-% acetic acid in water. In an embodiment, the present composition has an odor less unpleasant than (e.g., as measured by an hedonic tone rating) than 2 wt-% acetic acid in water. In an embodiment, the present composition has an odor with an odor less unpleasant than (e.g., as measured by an hedonic tone rating) than 1 wt-% acetic acid in water.

In an embodiment, the present compositions include medium chain peroxycarboxylic acid and include no, only insignificant, or relatively small amounts of short chain peroxycarboxylic acid, short chain carboxylic acid, or mixture thereof. For example, in an embodiment, the composition can be substantially free of added short chain carboxylic acid, short chain peroxycarboxylic acid, or mixture thereof. For example, in an embodiment, the composition can include short chain carboxylic acid, short chain peroxycarboxylic acid, or mixture thereof at a level insufficient to solubilize medium chain peroxycarboxylic acid. For example, in an embodiment, the composition can include short chain carboxylic acid, short chain peroxycarboxylic acid, or mixture thereof at a level insufficient to cause objectionable odor. For example, in an embodiment, the composition can include about 1 or more parts of medium chain peroxycarboxylic acid for each 8 parts of short chain carboxylic acid, short chain peroxycarboxylic acid, or mixture thereof.

Embodiments of the present invention include medium chain carboxylic acid and medium chain peroxycarboxylic acid, and certain embodiments specifically exclude short chain peroxycarboxylic acid, short chain carboxylic acid, or mixture thereof. Nonetheless embodiments of the present compositions can include short chain peroxycarboxylic acid, short chain carboxylic acid, or mixture thereof. It is not intended that addition of short chain peroxycarboxylic acid, short chain carboxylic acid, or mixture thereof to a composition should necessarily take a composition outside the spirit and scope of the present invention.

In certain embodiments including medium chain peroxycarboxylic acid, the present composition includes about 0.001 to about 30 wt-% oxidizing agent, about 0.001 to about 10 wt-% oxidizing agent, 0.002 to about 10 wt-% oxidizing agent, about 2 to about 30 wt-% oxidizing agent, about 2 to about 25 wt-% oxidizing agent, about 2 to about 20 wt-% oxidizing agent, about 4 to about 20 wt-% oxidizing agent, about 5 to about 10 wt-% oxidizing agent, or about 6 to about 10 wt-% oxidizing agent. The composition can include any of these ranges or amounts not modified by about.

In certain embodiments including medium chain peroxycarboxylic acid, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

In certain embodiments including medium chain peroxycarboxylic acid, the present composition includes about 0.001 to about 50 wt-% stabilizing agent, about 0.001 to about 5 wt-% stabilizing agent, about 0.5 to about 50 wt-% stabilizing agent, about 1 to about 50 wt-% stabilizing agent, about 1 to about 30 wt-% stabilizing agent, about 1 to about 10 wt-% stabilizing agent, about 1 to about 5 wt-% stabilizing agent, about 1 to about 3 wt-% stabilizing agent, about 2 to about 10 wt-% stabilizing agent, about 2 to about 5 wt-% stabilizing agent, or about 5 to about 15 wt-% stabilizing agent. The composition can include any of these ranges or amounts not modified by about.

Compositions Including Short Chain Carboxylic Acid and/or Peroxycarboxylic Acid

In certain embodiments, the compositions and methods of the invention can also include short chain peroxycarboxylic acids containing, for example, 2 to 4 carbon atoms. For example, short chain peroxycarboxylic (or percarboxylic) acids can have the formula $R(CO_3H)_n$, where R is a $C_2$-$C_4$ alkyl group and n is one or two. Short chain peroxycarboxylic acids useful in the compositions and methods of the present invention include peroxyacetic, peroxypropionoic, or peroxybutanoic acid, mixtures thereof, or the like. The alkyl backbones of the short chain peroxycarboxylic acids can be straight chain or branched. Peroxy forms of carboxylic acids with more than one carboxylate moiety can have one or more of the carboxyl moieties present as peroxycarboxyl moieties.

The short chain peroxycarboxylic acid can include or be a C2 to C4 peroxycarboxylic acid. The C6 to C12 peroxycarboxylic acid can include or be peroxyacetic acid, peroxypropionoic acid, peroxybutanoic acid, or mixture thereof. In an embodiment, the short chain peroxycarboxylic acid includes or is peroxyacetic acid. In certain embodiments, the present composition includes about 0.1 to about 25 wt-% short chain peroxycarboxylic acid, about 3 to about 20 wt-% short chain peroxycarboxylic acid, or about 5 to about 15 wt-% short chain peroxycarboxylic acid. The composition can include any of these ranges or amounts not modified by about.

The composition and methods of the invention can include short chain carboxylic acids containing, for example, 2 to 4 carbon atoms. For example, short chain carboxylic acids can have the formula R—COOH in which R can be a $C_2$-$C_4$ alkyl group. Suitable short chain carboxylic acids include acetic, propionic, or butanoic acid. The alkyl backbones of these short chain carboxylic acids can be straight chain, branched, or a mixture thereof. Carboxylic acids which are generally useful are those having one or two carboxyl groups where the R group is a primary alkyl chain having a length of $C_2$ to $C_4$. The primary alkyl chain is that carbon chain of the molecule having the greatest length of carbon atoms and directly appending carboxyl functional groups.

In an embodiment, the present compositions and methods include a short chain carboxylic acid. The short chain carboxylic acid can include or be a C2 to C4 carboxylic acid. The C6 to C12 carboxylic acid can include or be acetic acid, propionic acid, butanoic acid, or mixture thereof. In certain embodiments, the present composition includes about 0.1 to about 25 wt-% short chain peroxycarboxylic acid, about 3 to about 20 wt-% short chain peroxycarboxylic acid, or about 5 to about 15 wt-% short chain carboxylic acid. The composition can include any of these ranges or amounts not modified by about.

In an embodiment, the compositions and methods include a short chain peroxycarboxylic acid and the corresponding short chain carboxylic acid.

In an embodiment, the present composition includes an amount of short chain peroxycarboxylic acid ineffective for exhibiting antimicrobial activity or is substantially free of short chain peroxycarboxylic acid.

Carrier

The composition of the invention can also include a carrier. The carrier provides a medium which dissolves, suspends, or carries the other components of the composition. For example, the carrier can provide a medium for solubilization, suspension, or production of surfactant peroxycarboxylic acid and for forming an equilibrium mixture. The carrier can also function to deliver and wet the antimicrobial composition of the invention on an object. To this end, the carrier can contain any component or components that can facilitate these functions.

Generally, the carrier includes primarily water which can promote solubility and work as a medium for reaction and equilibrium. The carrier can include or be primarily an organic solvent, such as simple alkyl alcohols, e.g., ethanol, isopropanol, n-propanol, and the like. Polyols are also useful carriers, including glycerol, sorbitol, and the like.

Suitable carriers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™ FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™ Methyl PROPASOL™ acetate, Methyl PROPASOL™, Propyl CARBITOL™, Propyl CELLOSOLVE™, Propyl DIPROPASOL™ and Propyl PROPASOL™.

Generally, the carrier makes up a large portion of the composition of the invention and may be the balance of the composition apart from the active antimicrobial components, oxidizing agent, adjuvants, and the like. Here again, the carrier concentration and type will depend upon the nature of the composition as a whole, the environmental storage, and method of application including concentration of the surfactant peroxycarboxylic acid, among other factors. Notably the carrier should be chosen and used at a concentration which does not inhibit the antimicrobial efficacy of the surfactant peroxycarboxylic acid in the composition of the invention.

In certain embodiments, the present composition includes about 5 to about 90 wt-% carrier, about 10 to about 80 wt-% carrier, about 20 to about 40 wt-% carrier, or about 25 to about 35 wt-% carrier. The composition can include any of these ranges or amounts not modified by about.

Oxidizing Agent

The present compositions and methods can include any of a variety of oxidizing agents. The oxidizing agent can be used for maintaining or generating peroxycarboxylic acids.

Examples of inorganic oxidizing agents include the following types of compounds or sources of these compounds, or alkali metal salts including these types of compounds, or forming an adduct therewith:

hydrogen peroxide;

group 1 (IA) oxidizing agents, for example lithium peroxide, sodium peroxide, and the like;

group 2 (IIA) oxidizing agents, for example magnesium peroxide, calcium peroxide, strontium peroxide, barium peroxide, and the like;

group 12 (IIB) oxidizing agents, for example zinc peroxide, and the like;

group 13 (IIIA) oxidizing agents, for example boron compounds, such as perborates, for example sodium perborate hexahydrate of the formula $Na_2[Br_2(O_2)_2(OH)_4]\cdot 6H_2O$ (also called sodium perborate tetrahydrate and formerly written as $NaBO_3\cdot 4H_2O$); sodium peroxyborate tetrahydrate of the formula $Na_2Br_2(O_2)_2[(OH)_4]\cdot 4H_2O$ (also called sodium perborate trihydrate, and formerly written as $NaBO_3\cdot 3H_2O$); sodium peroxyborate of the formula $Na_2[B_2(O_2)_2(OH)_4]$ (also called sodium perborate monohydrate and formerly written as $NaBO_3\cdot H_2O$); and the like; in an embodiment, perborate;

group 14 (IVA) oxidizing agents, for example persilicates and peroxycarbonates, which are also called percarbonates, such as persilicates or peroxycarbonates of alkali metals; and the like; in an embodiment, percarbonate; in an embodiment, persilicate;

group 15 (VA) oxidizing agents, for example peroxynitrous acid and its salts; peroxyphosphoric acids and their salts, for example, perphosphates; and the like; in an embodiment, perphosphate;

group 16 (VIA) oxidizing agents, for example peroxysulfuric acids and their salts, such as peroxymonosulfuric and peroxydisulfuric acids, and their salts, such as persulfates, for example, sodium persulfate; and the like; in an embodiment, persulfate;

group VIIa oxidizing agents such as sodium periodate, potassium perchlorate and the like.

Other active inorganic oxygen compounds can include transition metal peroxides; and other such peroxygen compounds, and mixtures thereof.

In an embodiment, the compositions and methods of the present invention employ one or more of the inorganic oxidizing agents listed above. Suitable inorganic oxidizing agents include ozone, hydrogen peroxide, hydrogen peroxide adduct, group IIIA oxidizing agent, group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

Hydrogen peroxide presents one suitable example of an inorganic oxidizing agent. Hydrogen peroxide can be provided as a mixture of hydrogen peroxide and water, e.g., as liquid hydrogen peroxide in an aqueous solution. Hydrogen peroxide is commercially available at concentrations of 35%, 70%, and 90% in water. For safety, the 35% is commonly used. The present compositions can include, for example, about 2 to about 30 wt-% or about 5 to about 20 wt-% hydrogen peroxide.

In an embodiment, the inorganic oxidizing agent includes hydrogen peroxide adduct. For example, the inorganic oxidizing agent can include hydrogen peroxide, hydrogen peroxide adduct, or mixtures thereof. Any of a variety of hydrogen peroxide adducts are suitable for use in the present compositions and methods. For example, suitable hydrogen peroxide adducts include percarbonate salt, urea peroxide, peracetyl borate, an adduct of $H_2O_2$ and polyvinyl pyrrolidone, sodium percarbonate, potassium percarbonate, mixtures thereof, or the like. Suitable hydrogen peroxide adducts include percarbonate salt, urea peroxide, peracetyl borate, an adduct of $H_2O_2$ and polyvinyl pyrrolidone, or mixtures thereof. Suitable hydrogen peroxide adducts include sodium percarbonate, potassium percarbonate, or mixtures thereof, for example sodium percarbonate.

In an embodiment, the present compositions and methods can include hydrogen peroxide as oxidizing agent. Hydrogen peroxide in combination with the percarboxylic acid can provide certain antimicrobial action against microorganisms. Additionally, hydrogen peroxide can provide an effervescent action which can irrigate any surface to which it is applied. Hydrogen peroxide can work with a mechanical flushing action once applied which further cleans the surface of an object. An additional advantage of hydrogen peroxide is the food compatibility of this composition upon use and decomposition.

In certain embodiments, the present composition includes about 2 to about 50 wt-% oxidizing agent, about 5 to about 40 wt-% oxidizing agent, about 5 to about 30 wt-% oxidizing agent about 10 to about 20 wt-% oxidizing agent. The composition can include any of these ranges or amounts not modified by about.

Acidulant

In an embodiment, the present composition can include an acidulant. The acidulant can act as a catalyst for conversion of carboxylic acid to peroxycarboxylic acid. The acidulant can be effective to form a concentrate composition with pH of about 1 or less. The acidulant can be effective to form a use composition with pH of about 5, about 5 or less, about 4, about 4 or less, about 3, about 3 or less, about 2, about 2 or less, or the like. In an embodiment, the acidulant includes an inorganic acid. Suitable inorganic acids include sulfuric acid, phosphoric acid, nitric acid, hydrochloric acid, methane sulfonic acid, ethane sulfonic acid, propane sulfonic acid, butane sulfonic acid, xylene sulfonic acid, benzene sulfonic acid, mixtures thereof, or the like.

In an embodiment, the acidulant includes a carboxylic acid with $pK_a$ less than 4. Suitable carboxylic acids with $pK_a$ less than 4 include hydroxyacetic acid, hydroxypropionic acid, other hydroxycarboxylic acids, mixtures thereof, or the like.

In certain embodiments, the present composition includes about 10 to about 80 wt-% acidulant, about 20 to about 70 wt-% acidulant, about 30 to about 70 wt-% acidulant, about 35 to about 65 wt-% acidulant. The composition can include any of these ranges or amounts not modified by about.

Stabilizing Agent

One or more stabilizing agents can be added to the composition of the invention, for example, to stabilize the peracid and hydrogen peroxide and prevent the premature oxidation of this constituent within the composition of the invention.

Suitable stabilizing agents include chelating agents or sequestrants. Suitable sequestrants include organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, or aminocarboxylic acids.

The sequestrant can be or include phosphonic acid or phosphonate salt. Suitable phosphonic acids and phosphonate salts include 1-hydroxy ethylidene-1,1-diphosphonic acid ($CH_3C(PO_3H_2)_2OH$) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; or mixtures thereof.

Suitable organic phosphonates include HEDP.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), ($N[CH_2PO_3H_2]_3$), available from Monsanto as DEQUEST® 2000; ethylenediamind [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethyl-enediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0.2 to about 10 wt-% stabilizing agent, about 0.4 to about 4 wt-% stabilizing agent, about 0.6 to about 3 wt-% stabilizing agent, about 1 to about 2 wt-% stabilizing agent. The composition can include any of these ranges or amounts not modified by about.

Adjuvants

The antimicrobial composition of the invention can also include any number of adjuvants. Specifically, the composition of the invention can include wetting agent, defoaming agent, thickener, foaming agent, solidification agent, aesthetic enhancing agent (i.e., colorant (e.g., pigment), odorant, or perfume), among any number of constituents which can be added to the composition. Such adjuvants can be preformulated with the antimicrobial composition of the invention or added to the system simultaneously, or even after, the addition of the antimicrobial composition. The composition of the invention can also contain any number of other constituents as necessitated by the application, which are known and which can facilitate the activity of the present invention.

Wetting or Defoaming Agents

Also useful in the composition of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

In an embodiment, the present compositions can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, from about 0.01 wt-% to 2 wt-%, or from about 0.01 wt-% to about 1 wt-%.

Thickening or Gelling Agents

The present compositions can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, from about 0.1 wt-% to about 1.0 wt-%, or from about 0.1 wt-% to about 0.5 wt-%.

Solidification Agent

The present compositions can include a solidification agent, which can participate in maintaining the compositions in a solid form. In an embodiment, the solidification agent can form and/or maintain the composition as a solid. In an embodiment, the solidification agent can solidify the composition without unacceptably detracting from the eventual release of the surfactant peroxycarboxylic acid. The solidification agent can include, for example, an organic or inorganic solid compound having a neutral inert character or making a functional, stabilizing or detersive contribution to the present composition. Suitable solidification agents include solid polyethylene glycol (PEG), solid polypropylene glycol, solid EO/PO block copolymer, amide, urea (also known as carbamide), nonionic surfactant (which can be employed with a coupler), anionic surfactant, starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like;

Suitable glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like. Suitable solid polyethylene glycols are commercially available from Union Carbide under the tradename CARBOWAX.

Suitable amide solidification agents include stearic monoethanolamide, lauric diethanolamide, stearic diethanolamide, stearic monoethanol amide, cocodiethylene amide, an alkylamide, mixtures thereof, and the like. In an embodiment, the present composition can include glycol (e.g., PEG) and amide.

Suitable nonionic surfactant solidification agents include nonylphenol ethoxylate, linear alkyl alcohol ethoxylate, ethylene oxide/propylene oxide block copolymer, mixtures thereof, or the like. Suitable ethylene oxide/propylene oxide block copolymers include those sold under the Pluronic tradename (e.g., Pluronic 108 and Pluronic F68) and commercially available from BASF Corporation. In an embodiment, the nonionic surfactant can be selected to be solid at room temperature or the temperature at which the composition will be stored or used. In an embodiment, the nonionic surfactant can be selected to have reduced aqueous solubility in combination with the coupling agent. Suitable couplers that can be employed with the nonionic surfactant solidification agent include propylene glycol, polyethylene glycol, mixtures thereof, or the like.

Suitable anionic surfactant solidification agents include linear alkyl benzene sulfonate, alcohol sulfate, alcohol ether sulfate, alpha olefin sulfonate, mixtures thereof, and the like. In an embodiment, the anionic surfactant solidification agent is or includes linear alkyl benzene sulfonate. In an embodiment, the anionic surfactant can be selected to be solid at room temperature or the temperature at which the composition will be stored or used.

Suitable inorganic solidification agents include phosphate salt (e.g., alkali metal phosphate), sulfate salt (e.g., sodium sulfate or sodium bisulfate), acetate salt (e.g., anhydrous sodium acetate), carbonate salt (e.g., calcium carbonate or carbonate hydrate), other known hydratable compounds, mixtures thereof, and the like. In an embodiment, the inorganic solidification agent can include organic phosphonate compound and carbonate salt, such as an E-Form composition.

In an embodiment, the present composition can include any agent or combination of agents that provide a requisite degree of solidification and aqueous solubility can be included in the present compositions. In an embodiment, increasing the concentration of the solidification agent in the present composition can tend to increase the hardness of the composition. In an embodiment, decreasing the concentration of solidification agent can tend to loosen or soften the concentrate composition.

In an embodiment, the solidification agent can include any organic or inorganic compound that imparts a solid character to and/or controls the soluble character of the present composition, for example, when placed in an aqueous environment. For example, a solidifying agent can provide controlled dispensing if it has greater aqueous solubility compared to other ingredients in the composition. Urea can be one such solidification agent. By way of further example, for systems that can benefit from less aqueous solubility or a slower rate of dissolution, an organic nonionic or amide hardening agent may be appropriate.

In an embodiment, the present composition can include a solidification agent that provides for convenient processing or manufacture of the present composition. For example, the solidification agent can be selected to form a composition that can harden to a solid form under ambient temperatures of about 30 to about 50° C. after mixing ceases and the mixture is dispensed from the mixing system, within about 1 minute to about 3 hours, or about 2 minutes to about 2 hours, or about 5 minutes to about 1 hour.

The present composition can include solidification agent at any effective amount. The amount of solidification agent included in the present composition can vary according to the type of composition, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. Suitable amounts can include about 1 to about 90 wt-%, about 1.5 to about 85 wt-%, about 2 to about 80 wt-%, about 10 to about 45 wt-%, about 15% to about 40 wt-%, about 20% to about 30 wt-%, about 30% to about 70%, about 40% to about 60%, up to about 50 wt-%, about 40% to about 50%

Use Compositions

The present compositions include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the surfactant peroxycarboxylic acid compound. Generally, a dilution of about 1 fluid ounce to about 20 gallons of water to about 5 fluid ounces to about 1 gallon of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water.

For example, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent. Amounts of an ingredient in a use composition can be calculated from the amounts listed above for concentrate compositions and these dilution factors.

The present methods can employ surfactant peroxycarboxylic acid at a concentration effective for reducing the population of one or more microorganisms. Such effective concentrations include about 2 to about 500 ppm surfactant peroxycarboxylic acid, about 5 to about 200 ppm surfactant peroxycarboxylic acid, about 10 to about 100 ppm surfactant peroxycarboxylic acid, or about 20 to about 50 ppm surfactant peroxycarboxylic acid. In an embodiment, the use composition can include about 5 to about 200 ppm surfactant peroxycarboxylic acid, about 1 to about 1000 ppm carboxylic acid surfactant, and about 1 to about 99 wt-% carrier and/or diluent (e.g., water).

The level of reactive species, such as surfactant peroxycarboxylic acid and/or hydrogen peroxide, in a use composition can be affected, typically diminished, by organic matter that is found in or added to the use composition. For example, when the use composition is a bath or spray used for washing an object, soil on the object can consume peroxy acid and peroxide. Thus, the present amounts of ingredients in the use compositions refer to the composition before or early in use, with the understanding that the amounts will diminish as organic matter is added to the use composition.

Making Surfactant Peroxycarboxylic Acid Compositions

The compositions of or used in the methods of the invention can be made by combining or reacting the carboxylic acid surfactant and the oxidizing agent, such as hydrogen peroxide. Combining or reacting carboxylic acid surfactant and oxidizing agent results in production of surfactant peroxycarboxylic acid. In an embodiment, combining includes mixing. The formulation combined for making the present compositions can also include the acidulant, the carrier, stabilizing agent, mixtures thereof, or the like. Alternatively, one or more of the acidulant, the carrier, or mixtures thereof, can be added after production of some or all of the peroxycarboxylic acid.

In an embodiment, the present invention includes a method of making a surfactant peroxycarboxylic acid. The method can include combining or reacting carboxylic acid surfactant, carrier (e.g., water), oxidizing agent (e.g., hydrogen peroxide), acidulant, and stabilizing agent. The method can include mixing the ingredients at concentrations of about 1 to about 20 wt-% carboxylic acid surfactant, about 20 to about 80 wt-% carrier, about 20 to about 80 wt-% oxidizing agent, about 10 to about 50 wt-% acidulant, and about 1 to about 5 wt-% stabilizing agent. The present compositions also include compositions in which these combinations of ingredients have come to equilibrium forming surfactant peroxycarboxylic acid.

The present compositions can be made in a plant as a concentrate and shipped to an end user who need only dilute the concentrate to form a use composition. The present surfactant peroxycarboxylic acid compositions can also be made at the site of use. For example, the product can be shipped as a two or more part composition or as a kit. The user can then combine the two or more compositions or components of the kit to produce the present surfactant peroxycarboxylic acid compositions. Alternatively, a system of formulating equipment and containers of raw materials can be provided at the site of use, and programmed or operated to mix and disperse the present surfactant peroxycarboxylic acid compositions.

In an embodiment, the product can be supplied as a two or more part composition. One composition can include carboxylic acid surfactant and one or more of acidulant, carrier, stabilizing agent, mixtures thereof, or the like. The second composition can include oxidizing agent and one or more of acidulant, carrier, stabilizing agent mixtures thereof, or the like. Alternatively, the acidulant, carrier, stabilizing agent mixtures thereof, or the like can be supplied as additional composition(s).

In an embodiment, the pH of a concentrate composition can be less than about 1 or about 2. In an embodiment, the pH of a 1% or 1.5% solution of the mixture in water is about 1 or 2 to about 7, depending on the other components of the 1% solution. In an embodiment, the pH of a use composition can be from about 2 to about 7 depending on the other components.

Methods Employing the Surfactant Peroxycarboxylic Acid Compositions

The present invention includes methods employing the surfactant peroxycarboxylic acid compositions. Typically, these methods employ the antimicrobial or bleaching activity of the surfactant peroxycarboxylic acid. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a stabilized ester peroxycarboxylic acid composition of the invention. Contacting can include any of numerous methods for applying a composition, such as spraying the composition, immersing the object in the composition, foam or gel treating the object with the composition, or a combination thereof.

The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compositions can be employed as a foaming or nonfoaming environmental sanitizer or disinfectant.

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The antimicrobial compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people.

The present compositions can be employed for reducing the population of pathogenic microorganisms, such as pathogens of humans, animals, and the like. The compositions can exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a varieties of diseases and disorders, including mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The present composition is useful in the cleaning or sanitizing of containers, processing facilities, or equipment in the food service or food processing industries. The antimicrobial compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as *Legionella*.

The present compositions can be employed for reducing the population of microbes, fruit flies, or other insect larva on a drain or other surface.

The composition may also be employed by dipping food processing equipment into the use solution, soaking the equipment for a time sufficient to sanitize the equipment, and wiping or draining excess solution off the equipment, The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use solution is contacted with any of the above contaminated surfaces or items at use temperatures in the range of about 4° C. to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

The antimicrobial compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, foam or gel treating the object with the composition, or a combination thereof.

A concentrate or use concentration of a composition of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The composition can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compositions according to the invention, or solutions containing these compositions.

Clean in Place

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Generally, the actual cleaning of the in-place system or other surface (i.e., removal of unwanted offal therein) is accomplished with a different material such as a formulated detergent which is introduced with heated water. After this cleaning step, the instant composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, for example, about 30 to about 120 seconds. The present composition can remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity. These materials are useful at any conceivable temperatures.

A method of sanitizing substantially fixed in-place process facilities includes the following steps. The use solution of the invention is introduced into the process facilities at a temperature in the range of about 4° C. to 60° C. After introduction of the use solution, the solution is held in a container or circulated throughout the system for a time sufficient to sanitize the process facilities (i.e., to kill undesirable microorganisms). After the surfaces have been sanitized by means of the present composition, the use solution is drained. Upon completion of the sanitizing step, the system optionally may be rinsed with other materials such as potable water. The composition can be circulated through the process facilities for 10 minutes or less.

The present method can include delivering the present composition via air delivery to the clean-in-place or other surfaces such as those inside pipes and tanks. This method of air delivery can reduce the volume of solution required.

Contacting a Food Product with the Surfactant Peroxycarboxylic Acid Composition

The present method and system provide for contacting a food product with a surfactant peroxycarboxylic acid composition employing any method or apparatus suitable for applying such a composition. For example, the method and system of the invention can contact the food product with a spray of the composition, by immersion in the composition, by foam or gel treating with the composition, or the like. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the stabilized compositions of the invention to other objects.

The present methods require a certain minimal contact time of the composition with food product for occurrence of significant antimicrobial effect. The contact time can vary with concentration of the use composition, method of applying the use composition, temperature of the use composition, amount of soil on the food product, number of microorganisms on the food product, type of antimicrobial agent, or the like. The exposure time can be at least about 5 to about 15 seconds.

In an embodiment, the method for washing food product employs a pressure spray including the composition. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., for example, about 20 to 60° C. to increase efficacy. The spray stabilized composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compositions of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in a liquid stabilized composition can be accomplished by any of a variety of methods known to those of skill in the art. For example, the food product can be placed into a tank or bath containing the stabilized composition. Alternatively, the food product can be transported or processed in a flume of the stabilized composition. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the stabilized composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted foamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Methods for Beverage, Food, and Pharmaceutical Processing

The present surfactant peroxycarboxylic acid antimicrobial compositions can be used in the manufacture of beverage, food, and pharmaceutical materials including fruit juice, dairy products, malt beverages, soybean-based products, yogurts, baby foods, bottled water products, teas, cough medicines, drugs, and soft drinks. The materials can be used to sanitize, disinfect, act as a sporicide for, or sterilize bottles, pumps, lines, tanks and mixing equipment used in the manufacture of such beverages. Further, the surfactant peroxycarboxylic acid antimicrobial compositions can be used in aseptic, cold filling operations in which the interior of the food, beverage, or pharmaceutical container is sanitized or sterilized prior to filling. In such operations, a container can be contacted with the sanitizing surfactant peroxycarboxylic acid composition, typically using a spray, dipping, or filling device to intimately contact the inside of the container with the surfactant peroxycarboxylic acid composition, for sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill.

In food, beverage, or pharmaceutical manufacturing, fungal microorganisms of the genus *Chaetomium* or *Arthrinium*, and spores or bacteria of the genus *Bacillus* spp. can be a significant problem in bottling processes, particularly in cold aseptic bottling processes. The surfactant peroxycarboxylic acid sanitizer materials of the invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the surfactant peroxycarboxylic acid materials of the invention can be used to sanitize the interior of beverage containers prior to filling with the carbonated (or noncarbonated) beverage. Typical carbonated beverages in this application include cola beverage, fruit beverages, ginger ale beverages, root beer beverages, iced tea beverages which may be non-carbonated, and other common beverages considered soft drinks. The surfactant peroxycarboxylic acid materials of the invention can be used to sanitize both the tanks, lines, pumps, and other equipment used for the manufacture and storage of the soft drink material and also used in the bottling or containers for the beverages. In an embodiment, the surfactant peroxycarboxylic acid sanitizing materials are useful for killing both bacterial and fungal microorganisms that can be present on the surfaces of the production equipment and beverage containers.

The present invention is based upon the surprising discovery that surfactant peroxycarboxylic acid compositions can effectively kill microorganisms (e.g., >1 $\log_{10}$ or up to about 5 $\log_{10}$ reduction in 30 seconds) from a concentration level of at least about 150 part per million (ppm), for example, about 1000 ppm of surfactant peroxycarboxylic acid composition. In an embodiment, the surfactant peroxycarboxylic acid composition, excluding water, would be present at a concentration of about 0.001 to about 1 wt-%, for example, about 0.01 to about 0.15 wt-%, or about 0.05 to about 0.1 wt-%.

The FIGURE shows a schematic for an embodiment of a bottle spraying/bottling operation using surfactant peroxycarboxylic acid composition including a cold aseptic operation. In the FIGURE, a plant 100 that can contact beverage bottles with a surfactant peroxycarboxylic acid composition for a sanitizing regime is shown. In the FIGURE, bottles 110 are passed through a sterilizing tunnel 102. The sanitized bottles 110a then pass through a rinsing tunnel 103 and emerge as sanitized rinsed bottles 110b.

In the process, bulk surfactant peroxycarboxylic acid composition is added to a holding tank 101. Commonly, the materials are maintained at a temperature of about 22° C. in tank 101. To obtain the effective use concentration of the surfactant peroxycarboxylic acid composition, make-up water 105 is combined with the concentrated surfactant peroxycarboxylic acid composition in the tank 101. The surfactant peroxycarboxylic acid use composition can be passed through a heater 108 to reach a temperature of about 45-50° C. The heated surfactant peroxycarboxylic acid use composition can be sprayed within sterilizing tunnel 102 into and onto all surfaces of the bottle 110. An intimate contact between the surfactant peroxycarboxylic acid composition and the bottle 110 can be advantageous for reducing microbial populations to a sanitizing level.

After contact with the surfactant peroxycarboxylic acid use composition and after dumping any excess composition from the bottles, the sanitized bottles 110 are then passed to a fresh water rinse tunnel 103. Fresh water 108 is provided from a fresh water make-up into a spray rinsing tunnel 103. Excess spray drains from rinsing tunnel 103 to drain 106. Within the tunnel 103, sanitized bottles 110a can be thoroughly rinsed with fresh water. The complete removal of the surfactant peroxycarboxylic acid composition from the bottles 110a is important for maintaining high quality of the beverage product. The rinsed and sanitized bottles 110b are then removed from the rinsing tunnel.

The day tank 101, the sterilizing tunnel 102 and the rinsing tunnel 103 can be vented to wet scrubber or vent 111a, 111b or 111c to remove vapor or fumes from the system components. The sanitizer material that has been sprayed and drained from the bottles 110a accumulate in the bottom of the spray tunnel 102 and can then be recycled through recycle line and heater 107 into the day tank 101.

The day tank is used for diluting, storing, and delivering the surfactant peroxycarboxylic acid use composition which can include about 0.001 to about 1 wt-%, for example, about 0.01 to about 0.15 wt-%, or about 0.05 to about 0.1 wt-% surfactant peroxycarboxylic acid composition. All active treating equipment should be vented to a wet scrubber to prevent fumes from entering the atmosphere from the treatment equipment. Draining the containers of their surfactant peroxycarboxylic acid composition can reduce carry over minimized product loss. The contact between the bottles and the surfactant peroxycarboxylic acid antimicrobial composition is typically at a temperature of greater than about 0° C., more typically greater than 25° C., and most typically greater than about 40° C. Often temperatures between about 40° C. and 90° C. are used. To obtain sanitization or sterilization of beverage containers at about 150 ppm to about 1000 ppm surfactant peroxycarboxylic acid composition, contact at 40° C. to 60° C. for at least 5 sec, more preferably 10 sec, contact time is required.

Sanitizing or sterilizing conditions are greatly dependent on the processing temperatures, times, soil loading, water quality, and the like. In an embodiment, the sanitization equipment, day tank, sanitizing tunnel and rinsing tunnel are manufactured from polyolefin structural plastics, passivated stainless steel, or other non-corrosion sensitive production materials.

In the cold aseptic filling of 16 ounce polyethylene terephthalate (PET bottle), or other polymeric, beverage containers, a process has been adopted using a surfactant peroxycarboxylic acid composition. The surfactant peroxycarboxylic acid composition is diluted to a use concentration of about 0.1 to about 10 wt-% and is maintained at an effective elevated temperature of about 25° C. to about 70° C., preferably about 40° C. to about 60° C. The spray or flood of the bottle with the material ensures contact between the bottle and the sanitizer material for at least 5, e.g., 10, seconds. After flooding is complete, the bottle can be drained of all contents for a minimum of 2 seconds and optionally followed by a 5 second water rinse with sterilized water using about 200 milliliters of water at 38° C. (100° F.). If optionally filled with the rinse water, the bottle is then drained of the sterilized water rinse for at least 2 seconds and is immediately filled with liquid beverage. After the rinse is complete, the bottles usually maintain less than 10, preferably 3, milliliters of rinse water after draining.

The present invention may be better understood with reference to the following examples. These examples are intended to be representative of specific embodiments of the invention, and are not intended as limiting the scope of the invention.

EXAMPLES

Example 1

Compositions Including Surfactant Peroxycarboxylic Acid

Table 1 presents illustrative examples of the present compositions including surfactant peroxycarboxylic acid.

TABLE 1

| Ingredient | A | B | C | D | E | F |
|---|---|---|---|---|---|---|
| Surfactant Peroxycarboxylic Acid | — | — | — | 6 | 5 | 5 |
| Carboxylic Acid Surfactant | 7 | 6 | 6.4 | <1 | <1 | <1 |

TABLE 1-continued

Examples of Compositions

| | | | | | | |
|---|---|---|---|---|---|---|
| Carrier (e.g., water) | 37 | 38 | 38 | 37 | 38 | 38 |
| Oxidizing Agent (e.g., hydrogen peroxide) | 16 | 16 | 16 | 13 | 13 | 13 |
| Acidulant (e.g., sulfuric acid) | 38 | 38 | 38 | 38 | 38 | 38 |
| Stabilizing Agent (e.g., HEDP) | 2 | 1 | 1.5 | 2 | 1 | 1.5 |

| Ingredient | G | H | I | J | K | L | M | N |
|---|---|---|---|---|---|---|---|---|
| Surfactant Peroxycarboxylic Acid | — | — | — | — | 9 | 8 | 7 | 18 |
| Carboxylic Acid Surfactant | 10 | 9 | 8 | 19 | <1 | <1 | <1 | <1 |
| Carrier (e.g., water) | 18 | 18 | 18 | 15 | 18 | 18 | 18 | 15 |
| Oxidizing Agent (e.g., hydrogen peroxide) | 9 | 9 | 9 | 8 | 6 | 6 | 6 | 5 |
| Acidulant (e.g., sulfuric acid) | 61 | 62 | 63 | 56 | 61 | 62 | 63 | 56 |
| Stabilizing Agent (e.g., HEDP) | 1.5 | 1.5 | 1.5 | 1.5 | 1.5 | 1.5 | 1.5 | 1.5 |

Carboxylic acid surfactants formulated in compositions of the present invention include octyliminodipropionate (e.g., that sold under the trade name Mackam ODP (50% active)), aminopropionate (e.g., that sold under the trade name Mirataine JC HA (42% active), disodium laurethsulfosuccinate (e.g., that sold under the tradename Mackanate EL (39% active)), and linear alcohol ethoxycarboxylate (e.g., that sold under the tradename Neodox 23-4).

Example 2

Antimicrobial Efficacy of the Present Compositions Including Surfactant Peroxycarboxylic Acid Compositions according to the present invention were evaluated and demonstrated advantageous antimicrobial activity against microbes such as gram negative bacteria, gram positive bacteria, fungi, spores, viruses, and mycobacteria.

Materials and Methods

Antimicrobial activity was determined according to two well established methods. The first method was the procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). The second method was the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). Briefly, antimicrobial activity of the present compositions was determined by exposing a one mL aliquot containing the target microorganism to 99 mL of the desired concentration of the test substance at the desired temperature. After the specified contact time, one mL of the test solution containing the microorganism was neutralized and enumerated for survivors.

Results

The data shown in Tables 2 and 3 illustrate that the present surfactant peroxycarboxylic acid compositions effectively reduce the population of microorganisms such as *Staphylococcus aureus* and *Escherichia coli* in as little as 30 to 60 seconds at concentrations as low as 12-150 ppm.

TABLE 2

The Present Compositions Exhibit Antimicrobial Activity Against *S. aureus*.

| Surfactant Peroxycarboxylic Acid | ppm peroxycarboxylic acid | Exposure Time (sec) | Log Reduction |
|---|---|---|---|
| Octyliminodipropionate | 50 | 30 | 0.3 |
| (Mackam ODP) | 50 | 60 | 0.5 |
| | 250 | 30 | 0.4 |
| | 250 | 60 | >7 |
| Aminopropionate | 50 | 30 | 0.5 |
| (Mirataine JC HA) | 50 | 60 | 0.8 |
| | 250 | 30 | 6.1 |
| | 250 | 60 | >7 |
| Disodium | 50 | 30 | 1.6 |
| Laurethsulfosuccinate | 50 | 60 | 1.9 |
| (Mackanate EL) | 250 | 30 | 3.1 |
| | 250 | 60 | >6.1 |
| Linear Alcohol | 50 | 30 | 2.2 |
| Ethoxycarboxylate | 50 | 60 | 2.4 |
| (Neodox 23-4) | 250 | 30 | 4.8 |
| | 250 | 60 | >4.6 |

TABLE 3

The Present Compositions Exhibit Antimicrobial Activity Against *E. coli*.

| Surfactant Peroxycarboxylic Acid | ppm peroxycarboxylic acid | Exposure Time (sec) | Log Reduction |
|---|---|---|---|
| Octyliminodipropionate | 50 | 30 | 0.7 |
| (Mackam ODP) | 50 | 60 | 2 |
| | 250 | 30 | >7.2 |
| | 250 | 60 | >7.2 |
| Aminopropionate | 50 | 30 | 1.7 |
| (Mirataine JC HA) | 50 | 60 | >7.2 |
| | 250 | 30 | >7.2 |
| | 250 | 60 | >7.2 |
| Disodium | 50 | 30 | 0.6 |
| Laurethsulfosuccinate | 50 | 60 | 3.4 |
| (Mackanate EL) | 250 | 30 | >7.2 |
| | 250 | 60 | 7.1 |
| Linear Alcohol | 50 | 30 | 5.8 |
| Ethoxycarboxylate | 50 | 60 | >7.2 |
| (Neodox 23-4) | 250 | 30 | >7.2 |
| | 250 | 60 | >7.2 |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A composition comprising:
    an effective antimicrobial amount of surfactant peroxycarboxylic acid, wherein the surfactant peroxycarboxylic acid comprises anionic surfactant peroxycarboxylic acid, amphoteric surfactant peroxycarboxylic acid, zwitterionic surfactant peroxycarboxylic acid, or mixture thereof; wherein the surfactant peroxycarboxylic acid comprises one or more of an alkyl carboxylate moiety, an alkyl amide moiety, an alkyl sulfonate moiety, an ethoxylate moiety, or a propoxylate moiety;
    about 0.0005 to about 40 wt-% carboxylic acid surfactant;
    an oxidizing agent; and
    about 20 wt-% to 70 wt-% of an acidulant.

2. The composition of claim 1, comprising: about 0.0005 to about 15 wt-% surfactant peroxycarboxylic acid; and about 0.0005 to about 25 wt-% carboxylic acid surfactant.

3. The composition of claim 1, wherein the oxidizing agent comprises about 0.0005 to about 50 wt-% of the composition.

4. The composition of claim 1, wherein the acidulant comprises about 30 wt-% to about 70 wt-% of the composition.

5. The composition of claim 1, further comprising about 0.00002 to about 10 wt-% stabilizing agent.

6. The composition of claim 1, further comprising about 5 to about 99.9999 wt-% carrier.

7. The composition of claim 1, wherein the surfactant peroxycarboxylic acid is selected from the group consisting of an alcohol ethoxy peroxycarboxylic acid, a sulfo peroxysuccinic acid, an alkylamine peroxycarboxylic acid, or mixture thereof.

8. The composition of claim 7, wherein the surfactant peroxycarboxylic acid comprises an alcohol ethoxy peroxycarboxylic acid.

9. The composition of claim 8, Wherein the surfactant peroxycarboxylic acid comprises a linear alcohol ethoxy peroxycarboxylic acid.

10. The composition of claim 7, wherein the surfactant peroxycarboxylic acid comprises sulfo peroxysuccinic acid.

11. The composition of claim 10, wherein the surfactant peroxycarboxylic acid comprises laurethsulfoperoxysuccinic acid.

12. The composition of claim 7, wherein the surfactant peroxycarboxylic acid comprises an alkylamine peroxycarboxylic acid.

13. The composition of claim 12, wherein the surfactant peroxycarboxylic acid comprises alkyliminodipropionate peroxycarboxylic acid.

14. The composition of claim 13, wherein the surfactant peroxycarboxylic acid comprises linear alcohol ethoxy peroxycarboxylic acid, laurethsulfoperoxysuccinic acid, alkyliminodipropionate peroxycarboxylic acid, or mixture thereof.

15. The composition of claim 1, wherein the carboxylic acid surfactant comprises an anionic surfactant, an amphoteric surfactant, a zwitterionic surfactant, or a mixture thereof.

16. The composition of claim 15, wherein the carboxylic acid surfactant comprises an alcohol ethoxycarboxylate.

17. The composition of claim 16, wherein the carboxylic acid surfactant comprises a linear alcohol ethoxycarboxylate.

18. The composition of claim 15, wherein the carboxylic acid surfactant comprises sulfosuccinate.

19. The composition of claim 18, wherein the carboxylic acid surfactant comprises laurethsulfosuccinate.

20. The composition of claim 15, wherein the carboxylic acid surfactant comprises an alkylaminecarboxylate.

21. The composition of claim 20, wherein the carboxylic acid surfactant comprises alkyliminodipropionate.

22. The composition of claim 15, wherein the carboxylic acid surfactant comprises linear alcohol ethoxycarboxylate, laurethsulfosuccinate, alkyliminodipropionate, or mixture thereof.

23. A method of reducing population of microorganism on an object, the method comprising:
contacting the object with a surfactant peroxycarboxylic acid composition;
the composition comprising:
an effective antimicrobial amount of surfactant peroxycarboxylic acid, wherein the surfactant peroxycarboxylic acid comprises anionic surfactant peroxycarboxylic acid, amphoteric surfactant peroxycarboxylic acid, zwitterionic surfactant peroxycarboxylic acid, or mixture thereof;
about 0.0005 to about 40 wt-% of a carboxylic acid surfactant;
an oxidizing agent; and
about 20 wt-% to 70 wt-% of an acidulant.

24. An article of manufacture comprising:
a first composition comprising carboxylic acid surfactant and carrier;
a second composition comprising oxidizing agent;
directions for combining the first and second compositions;
wherein combining the first and second compositions provides a surfactant peroxycarboxylic acid composition:
the surfactant peroxycarboxylic acid composition comprising:
an effective antimicrobial amount of surfactant peroxycarboxylic acid, wherein the surfactant peroxycarboxylic acid comprises anionic surfactant peroxycarboxylic acid, amphoteric surfactant peroxycarboxylic acid, zwitterionic surfactant peroxycarboxylic acid, or mixture thereof;
about 0.0005 to about 40 wt-% of the carboxylic acid surfactant;
an oxidizing agent; and
about 20 wt-% to 70 wt-% of an acidulant.

* * * * *